(12) United States Patent
George et al.

(10) Patent No.: US 9,504,427 B2
(45) Date of Patent: Nov. 29, 2016

(54) SIGNAL AVERAGING

(75) Inventors: Brian P. George, Medina, OH (US); Remi Dubois, Paris (FR); Charulatha Ramanathan, Solon, OH (US); Harold Wodlinger, Thornhill (CA)

(73) Assignee: Cardioinsight Technologies, Inc., Cleveland, OH (US)

( * ) Notice: Subject to any disclaimer, the term of this patent is extended or adjusted under 35 U.S.C. 154(b) by 178 days.

(21) Appl. No.: 14/115,235

(22) PCT Filed: May 4, 2012

(86) PCT No.: PCT/US2012/036543
§ 371 (c)(1),
(2), (4) Date: Nov. 1, 2013

(87) PCT Pub. No.: WO2012/151498
PCT Pub. Date: Nov. 8, 2012

(65) Prior Publication Data
US 2014/0067279 A1 Mar. 6, 2014

Related U.S. Application Data

(60) Provisional application No. 61/482,345, filed on May 4, 2011.

(51) Int. Cl.
| | | |
|---|---|---|
| *G01N 33/48* | (2006.01) | |
| *A61B 5/00* | (2006.01) | |
| *A61B 5/0402* | (2006.01) | |
| *A61B 5/0452* | (2006.01) | |
| *G06K 9/00* | (2006.01) | |
| *G06G 7/58* | (2006.01) | |
| *A61B 5/0408* | (2006.01) | |
| *A61B 5/042* | (2006.01) | |

(52) U.S. Cl.
CPC ......... *A61B 5/7235* (2013.01); *A61B 5/04028* (2013.01); *A61B 5/04525* (2013.01); *A61B 5/7203* (2013.01); *A61B 5/7278* (2013.01); *G06K 9/0051* (2013.01); *G06K 9/00543* (2013.01); *A61B 5/0422* (2013.01); *A61B 5/04085* (2013.01); *A61B 5/7221* (2013.01)

(58) Field of Classification Search
None
See application file for complete search history.

(56) References Cited

U.S. PATENT DOCUMENTS

| | | |
|---|---|---|
| 4,630,204 A | 12/1986 | Mortara |
| 5,139,027 A | 8/1992 | Lindercrantz |
| 5,628,326 A | 5/1997 | Arand et al. |
| 5,682,900 A | 11/1997 | Arand et al. |
| 5,704,365 A | 1/1998 | Albrecht et al. |
| 5,840,038 A | 11/1998 | Xue et al. |
| 7,502,643 B2 | 3/2009 | Farringdon et al. |
| 7,706,866 B2 | 4/2010 | Zhang et al. |
| 7,912,535 B2 | 3/2011 | Couderc et al. |
| 2006/0235322 A1 | 10/2006 | Simske et al. |
| 2008/0058657 A1 | 3/2008 | Schwartz et al. |
| 2008/0132799 A1 | 6/2008 | Xue |
| 2008/0183093 A1 | 7/2008 | Duann et al. |
| 2009/0216146 A1 | 8/2009 | Teicher et al. |
| 2010/0179444 A1 | 7/2010 | O'Brien et al. |
| 2010/0217144 A1 | 8/2010 | Brian |

FOREIGN PATENT DOCUMENTS

| | | |
|---|---|---|
| JP | 62217936 A | 9/1987 |
| JP | 6125883 A | 5/1994 |
| JP | 2005323821 A | 11/2005 |
| JP | 2008068084 A | 3/2008 |
| JP | 2010510851 | 4/2010 |
| JP | 2011530388 A | 12/2011 |
| JP | 2012508079 A5 | 12/2012 |
| JP | 05197767 B2 | 5/2013 |
| WO | 2010019494 A1 | 2/2010 |
| WO | 2010054409 A1 | 5/2010 |

OTHER PUBLICATIONS

F. Castells, et al., Estimation of Atrial Fibrillatory Waves From One-Lead ECGs Using Principal Component Analysis Concepts, Computers in Cardiology, IEEE, 2004, pp. 413-416.
Japanese Patent Application No. 2014-535919; Office Action Mailing (English Translation) Date: Jun. 2, 2015; pp. 1-5.
Int'l Search Report and Written Opinion—9 pgs., Nov. 23, 2012, CardioInsight Technolgoies, Inc.
J. I. Aunon, et al., "Comparison of Different Techniques for Processing Evoked Potentials", Medical Biological Engineering & Computing, Nov. 1978, 9 pp.
E. Zoghlami Ayari, et al., "Low Power Electrocardiogram QRS Detection in Real-Time", ICBME 2008, Proceedings 23, pp. 643-646, Jan. 2009 www.springerlink.com.

(Continued)

*Primary Examiner* — Eric S Dejong
(74) *Attorney, Agent, or Firm* — Tarolli, Sundheim, Covell & Tummino LLP

(57) ABSTRACT

A method (500) can comprise performing principal component analysis (PCA) on data corresponding to a subset of a plurality of signals and a selected template to generate a virtual lead and an optimized template (530). The method can also comprise calculating a cross correlation on the virtual lead and the optimized template to determine a strength of linear dependence between the virtual lead and the optimized template to determine regions of interest (ROIs) of the virtual lead (540). The method can further comprise detecting peak correlation coefficients in the virtual lead (550). The method can still further comprise comparing the amplitude of each of the ROIs of the virtual lead with the selected template to determine an error between the template and each ROI of the virtual lead (560). The method can yet further comprise averaging the ROIs to generate averaged data (570).

20 Claims, 16 Drawing Sheets

(56) References Cited

OTHER PUBLICATIONS

Jane Kantelhardt, PhD, et al., "Bivariate Phase-Rectified Signal Averaging—a novel technique for cross-correlation analysis in noisy nonstationary signals", ScienceDirect, Journal of Electrocardiology 42, Aug. 2009, pp. 602-606.

Clay L. Birkett, et al., "A Signal-Averaging Technique for the Analysis of Human Muscle Sympathetic Nerve Activity", the American Physiological Society, Jul. 1992, 6 pp.

Szi-Wen Chen, et al., "A Real-time QRS Detection Method Based on Moving-Averaging Incorporating with Wavelet Denoising", Elsevier Health, Computer Methods and Programs in Biomedicine 82 Jun. 2006 pp. 187-195.

Ivaylo I Christov, "Real Time Electrocardiogram QRS Detection Using Combined Adaptive Threshold", BioMedical Engineering OnLine, Aug. 27, 2004, pp. 1-9.

Dawood Darbar, et al., "Prolonged Signal-Averaged P-Wave Duration as an Intermediate Phenotype for Familial Atrial Fibrillation", Journal of the American College of Cardiology, vol. 51, No. 11, Mar. 2008, 9 pp.

GE Medical Systems—Information Technologies, "Signal-Averaged High Resolution P-Wave (PHI-RES) Analysis", (2001), 2 pp.

Fredrik Holmqvist, et al., "Signal-Averaged P Wave Analysis for Delineation of Interatrial Conduction—Further Validation of the Method", BMC Cardiovascular Disorders BioMed Central, Oct. 9, 2007, pp. 1-8.

E.H. Hon, et al., "Averaging Techniques in Fetal Electrocardiography", Med. Electron, Biol. Engng. vol. 2, Mar. 1964, pp. 71-76.

Steven L. Horner, et al., "Real-time Signal Processing of an Intrauterine Catheter's Fetal Electrocardiogram", Digital Signal Processing, Apr. 2003 pp. 368-395.

Ivo Iliev, et al., "Real-time Detection of Pathological Cardiac Events in the Electrocardiogram", Physiological Measurement, IOP Publishing Ltd, Feb. 9, 2007, 18 pp.

M. Sasha John, et al., "Weighted Averaging of Steady-State Responses", Elsevier Science Ireland Ltd., Mar. 2001, 8 pp.

Jan W. Kantelhardt, et al., "Phase-Rectified Signal Averaging for the Detection of Quasi-Periodicities and the Prediction of Cardiovascular Risk", American Institute of Physics, Chaos, Mar. 2007, 9 pp.

Thorsten Last, et al., "Multi-Component Based Cross Correlation Beat Detection in Electrocardiogram Analysis", BioMed Central, Jul. 23, 2004, pp. 1-14.

Nicos Maglaveras, et al., "ECG Pattern Recognition and Classification Using non-linear Transformations and Neural Networks: A review", Elsevier Science Ireland Ltd., Oct. 1998, 18 pp.

Antonio Michelucci, et al., "P Wave Assessment: State of the Art Update", Cardiac Electrophysiology Review, Sep. 2002, 6 pp.

Anthony W. Nathan, et al., "Noninvasive Recording of the His Bundle Electrogram in Neonates", Pediatric Cardiology, Jan. 1984, 6 pp.

Kiapu Pan, et al., "A Real-Time QRS Detection Algorithm", IEEE Transactions on Biomedical Engineering, vol. BME-32, No. 3, Mar. 3, 1985, 9 pp.

J. Peregrin, et al., "Averaging, Selective Averaging and Latency-Corrected Averaging", Pflügers Archiv European Journal of Physiology, Aug. 1981, 5 pp.

"Signal and noise in Measurement", sigavg__6.mcd, May 31, 1997, 4 pp.

P. Trahanias, et al., "Bottom-up Approach to the ECG Pattern-Recognition Problem", Medical & Biological Engineering & Computing, May 1989, 9 pp.

Yong Wang, et al., "Noninvasive Electroanatomic Mapping of Human Ventricular Arrhythmias with Electrocardiographic Imaging (ECGI)", Science of Translational Medicine, Sep. 1, 2011, 60 pp.

David J. Wilber, MD, "Electrocardiographic Imaging: New Tool for Interventional Electrophysiology, or just another pretty picture?", Editorial Commentary, Heart Rhythm Society, Jun. 2007, 2 pp.

Yun-Chi Yeh, et al., "QRS Complexes Detection for ECG Signal: The Difference Operation Method", Elsevier Ireland Ltd., (2008), Apr. 17, 2008, 10 pp.

Wang, et al., "Application of the Method of Fundamental Solutions to Potential-based Inverse Electrocardiography"; Annals of Biomedical Engineering, vol. 34, No. 8, Aug. 2006; pp. 1272-1288.

Lyons, "Understanding Digital Signal Processing: Second Edition"; Upper Saddle River: Prentice Hall; Copyright 2004; pp. 411-438.

Northrop, R., "Signals and Systems Analysis in Biomedical Engineering"; Boca Raton: CRC Press; Copyright 2003; pp. 256-265.

SIGNAL AVERAGING

RELATED APPLICATIONS

This application claims the benefit of priority to U.S. Provisional Application No. 61/482,345, entitled "SIGNAL AVERAGING," and filed on May 4, 2011, which is incorporated herein by reference in its entirety.

TECHNICAL FIELD

This disclosure relates to systems and methods for averaging a plurality of signals, such as may be used for assessing a biological condition.

BACKGROUND

When an electrophysiological signal is sensed, the sensed signal can be contaminated with interfering noise from various sources. For the example of electrocardiogram (ECG) signals, sources of the noise can be a combination one or more of the following: electromagnetic radiation (e.g., about 50 Hz or 60 Hz depending on the country and harmonics) which include radio transmission, electrical wires, fluorescent lights; motion artifacts and baseline drift (e.g., ranging from about 0 Hz to about 20 Hz); electromyographic noise (e.g., ranging from about 20 Hz to about 200 Hz); and other electrophysiological equipment (e.g., generally ranging from about 0 Hz to about 2000 Hz). Given that the diagnostic frequency spectrum of ECGs can range from about 0.5 Hz to about 100 Hz, the presence of the noise can make a physician's analysis and diagnostic interpretation of the data difficult, especially when the sensed signals are low voltage signals (e.g., less than about 50 $\mu V$).

A common and simple post-analysis method to remove contamination noise is to use a digital filter. For example, a band pass digital filter can eliminate both high and low frequency noise and only allow the desired frequencies to pass. However, the frequency response of a narrow frequency band filter may also remove physiologically relevant frequencies of the ECG signal. Another approach is to use a signal averaging technique which is commonly used in signal-averaged electrocardiography. The method may reduce small amounts of interfering noise, but cannot process large amount of noise or variations within the ECG signal.

SUMMARY

One example is related to a method comprising performing principal component analysis (PCA) on data corresponding to a subset of a plurality of signals and a selected template to generate a virtual lead and an optimized template. Each of the plurality of signals can correspond to an electrical biological signal detected by a sensor. The method can also comprise calculating a cross correlation on the virtual lead and the optimized template to determine a strength of linear dependence between the virtual lead and the optimized template to determine regions of interest (ROIs) of the virtual lead. The method can further comprise detecting peak correlation coefficients in the virtual lead. The method can yet further comprise comparing the amplitude of each of the ROIs of the virtual lead with the selected template to determine an error between the template and each ROI of the virtual lead. The method can still yet further comprise averaging the ROIs to generate averaged data.

Another example relates to a non-transitory machine readable medium for storing machine readable instructions. The machine readable instructions can comprise a signal averager configured to receive measurement data that characterizes a plurality of detected biological signals. The signal averager can comprise a PCA function configured to perform PCA on the measurement data for a subset of the detected biological signals and a selected template to generate a virtual lead and an optimized template. The signal averager can also comprise a cross correlation (CC) calculator configured to determine a strength of linear dependence between the virtual lead and the optimized template to determine ROIs of the virtual lead. The signal averager can further comprise an amplitude comparator configured to compare the amplitude of each of the ROIs of the virtual lead with the selected template to determine an error between the template and each ROI of the virtual lead. The signal averager can still further comprise a segment averaging function configured to average each of the ROIs to calculate averaged data (e.g., for each of the biological signals).

Yet another example can relate to a system comprising a memory for storing machine readable instructions and a processing unit to access the memory and execute the machine readable instructions. The machine readable instructions can comprise a signal averager configured to detect regions of poor signal quality for each of a plurality of signals, wherein each of the plurality of signals corresponds to a biological signal. The signal averager can also be configured to determine which of the plurality of signals is associated with a bad channel based on the detected regions of poor signal quality. The signal averager can still further be configured to provide averaged data corresponding to an average of ROIs that are determined based on a strength of linear dependence between a virtual lead and an optimized template, wherein the virtual lead and the optimized template are based on the plurality of signals that are not associated with the bad channel and based on a selected template.

DETAILED DESCRIPTION

This disclosure relates to signal averaging for detected biological electrical signals. The signal averaging systems and methods provide an efficient approach for reducing the noise and preserve integrity of signal.

For example, ECG signals can be contaminated by interfering noise, whether from other lab equipment (computers) or the patient (electromyographic noise). The presence of the noise can make analysis and diagnostic interpretation of the data difficult, especially when the signals are low in voltage since the noise can overshadow the signal and prevent detection. Along with reducing the amount of interfering noise, the systems and methods disclosed herein can help accentuate and bring out small, but highly key signals that may be of diagnostic importance.

This disclosure provides signal averaging operative to reduce noise and enable low amplitude signal detection, such as body surface electrical activity. As an example, the signal averaging disclosed herein can encompass detection of local and global signal quality, data optimization by a principal component analysis, template matching by cross correlation, accurate matching by peak correlation detection and amplitude comparison, and ensemble averaging over all input channels, such as by using signal quality discrimination methods. The approach disclosed herein can also mitigate the number of false detections with a high accuracy of template detection, which can result in higher signal quality. As another example, by utilizing the signal averaging approach disclosed herein, signals as small as about 3 μV or less could be detected depending on the varying noise level. It will be appreciated that the signal averaging approach can be utilized to improve and advance the performance and accuracy of the detection method while preserving the noise reduction procedure.

For ease of explanation, examples of the signal averaging systems and methods are disclosed herein in the context of electrocardiogram (ECG) signals. It will be understood and appreciated that the systems and methods are equally applicable to other types of sensed electrical signals, including other types of electrophysiological signals (e.g., electromyography, electroencephalography, electrooculography, audiology and the like) as well as non-physiological electrical signals.

Figure 1:
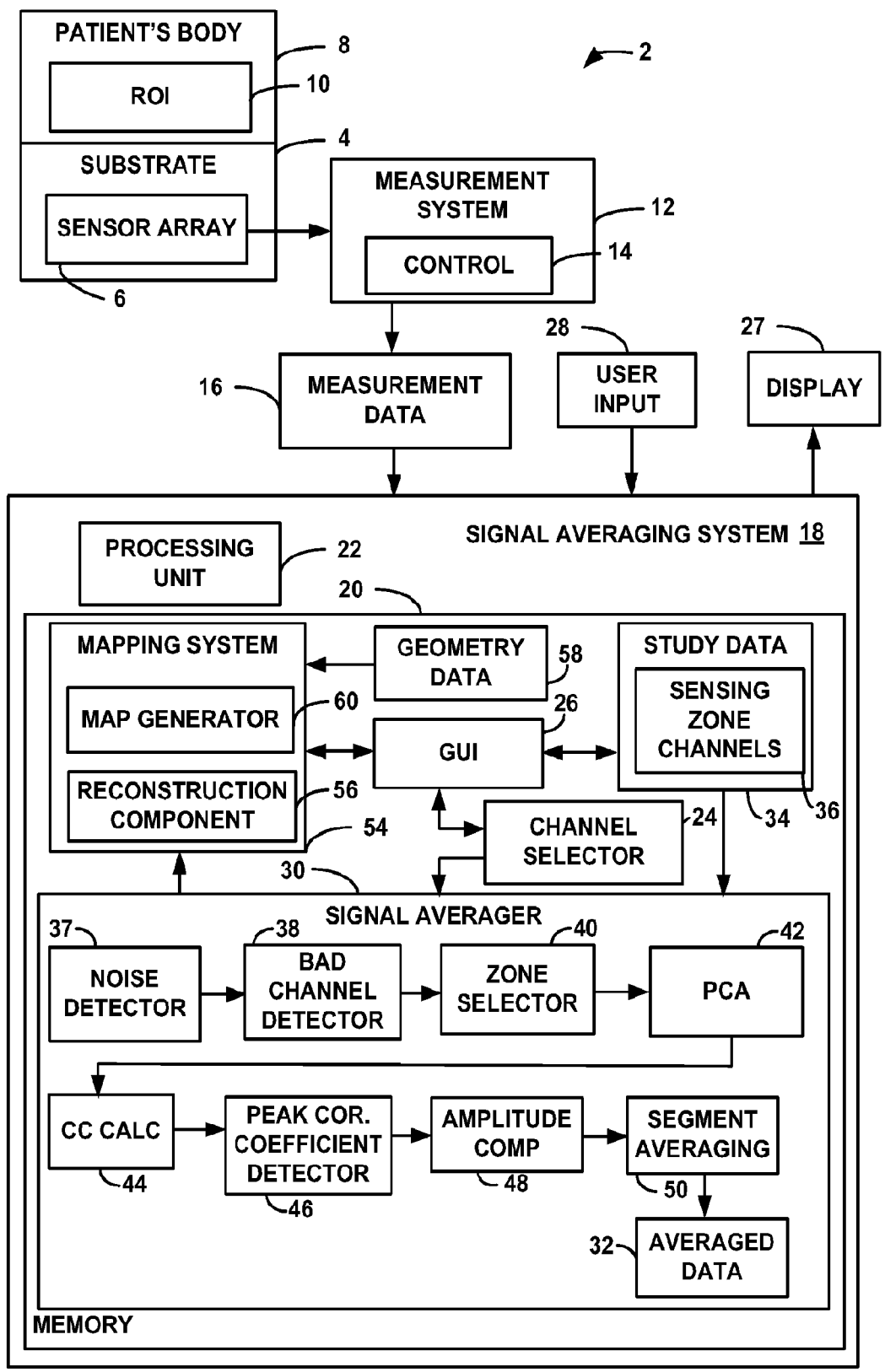
FIG. 1 illustrates an example of a system for signal averaging.

FIG. 1 illustrates an example of a system 2 that can be employed to process detected biological signals, such as ECG, EEG, EMG, EOG signals or the like. The system 2 can include a substrate 4 with a sensor array 6 mounted thereon. The substrate 4 could be implemented, for example, as a patient vest, a patient helmet or the like. The substrate 4 can be in physical contact with a patient's body 8. Alternatively, the sensors 6 can be connected to the patient's body 8 without using a substrate.

Sensors in the sensor array 6 can be spaced apart in a distributed arrangement to detect the biological signals at different positions of the patient's body 8. Each of the sensors could be implemented, for example, as an electrode that can be utilized for recording patient electrical activity of a region of interest (ROI) 10, such as a heart or a brain of the patient. In some examples, the sensor array 6 can include non-invasive sensors that are attached to an external surface of the patient's body 8, such as the torso or head. Additionally or alternatively, the sensor array 6 could include invasive sensors that are positioned at the region of interest within the patient's body 8. In some examples, there can be about 200 or more sensors (e.g., about 252 sensors) in the sensor array 6. The number of sensors can vary according to application requirements.

The signals detected by the sensor array 6 can be referred to as detected signals. The detected signals can be provided to a measurement system 12. The measurement system 12 can include a control 14 which can be implemented as hardware and/or software for providing corresponding measurement data 16 that characterizes electrical signals detected by each of the sensors in the sensor array 6. The measurement data 16 can be stored in memory as analog or digital information. Appropriate timestamps can be utilized for indexing the temporal relationship between the respective measurement data 16 to facilitate the evaluation and analysis thereof. The measurement data 16 can be provided to a signal analysis system 18.

In the example of FIG. 1, the signal analysis system 18 can be implemented as a computer, such as a laptop computer, a desktop computer, a server, a tablet computer, a workstation or the like. The signal analysis system 18 can include a memory 20 for storing data and machine-readable instructions. While the measurement data 16 is demonstrated as being external to the analysis system 18, such data could be stored in the memory 20 of the analysis system. The memory 20 could be implemented, for example, as a non-transitory computer storage medium, such as volatile memory (e.g., random access memory), non-volatile memory (e.g., a hard disk drive, a solid-state drive, flash memory or the like) or a combination thereof.

The signal analysis system 18 can also include a processing unit 22 to access the memory 20 and execute the machine-readable instructions stored in the memory. The processing unit 22 could be implemented, for example, as one or more processor cores. In the present examples, although the components of the signal analysis system 18 are illustrated as being implemented on the same system, in other examples, the different components could be distributed across different systems and communicate, for example, over a network.

By way of example, the measurement data 16 can be provided to a channel selector 24 stored in the memory 20. The channel selector 24 can, for example, be employed to select a template region (e.g., corresponding to P wave or identifiable portion) of detected signals characterized in the measurement data 16. In some examples, the channel selector 24 can interface with a graphical user interface (GUI) 26 stored in the memory 20, such that the template region can be selected in response to user input 28. Additionally, the GUI 26 can provide data to a display 27 sufficient to provide a graphical representation (e.g., a chart) corresponding to each (or a selected subset) of the detected signals included in the measurement data 16, such as to facilitate selecting the template region.

The selected template region can be provided to a signal averager 30 that is stored in the memory 20. The signal averager 30 can be programmed to employ processing methods, such as those disclosed herein to provide averaged data 32 for each of the detected input signal signals based on the detected signals in the template region. The number of input signals (corresponding to input channels) can depend on the configuration of the sensor array 6, and averaging is performed in relation to each such input channel (excluding bad channels), for example. The signal averager 30 can be programmed to perform data pre-processing to determine localized signal quality as well as global signal quality per channel can be implemented.

In one example, the GUI 26 can select study data 34 for a given study in response to user input 28. The study data can characterize a particular type of biological study to perform on the patient. For instance, in some examples, the given study could be an atrial study, a ventricle study or the like. In other examples, the study data can identify one or more different anatomical regions of interest, which can be selected in response to user input or automatically according to other preselected analysis criteria. In any case, the study data can include information that identifies a subset of the sensors (or nodes) in the sensor array 6 for the selected study, which subset can collectively referred to as sensing zone channels 36. In some examples, the subset of the sensors could be a proper subset of the sensors in the sensor array 6, while in other examples, the subset can include all of the sensors in the sensor array 6. The sensing zone channels 36 could be predefined for a given type of study as represented by the study data 34. Alternatively or additionally, the sensing zone channels 36 could be determined based on an analysis of the patient and/or the sensor array 6 in response to a user input. The study data 34 can also be provided to the signal averager 30.

The signal averager 30 can include a noise detector 37 that can detect and remove correlated noise (e.g., ambient noise from a power line). The noise detector 37 can be implemented in the measurement system as another example. In some examples, the noise detector 37 can be implemented as a low pass filter. The output of the noise detector 37 can be provided to a bad channel detector 38.

The bad channel detector 38 can be implemented to detect a bad channel. The bad channel detector 38 can identify a channel as a "bad channel" upon determining, for example, if all of the data points in the channel are zero or if about 75% or more of the signal for such channel is to be deemed to have a poor signal quality. The bad channels identified by the bad channel detector 38 can be provided to a zone selector 40 of the signal averager 30. The zone selector 40 can selects a zone corresponding to the subset of sensing zone channels 36 included in the study data 34 and excludes the bad channel. The selected zone and identified bad channels can be provided to a principal component analysis (PCA) function 42 of the signal averager 30. As mentioned above, the selected zone can include a proper subset of the input channels or it can include up to all input channels. In some examples, bad channels may reside within the selected zone or they may be outside of the selected zone. In this latter case, the bad channel may be excluded from use by the PCA function 42 without affecting the PCA. If one or more bad channels reside within the selected zone, the bad channels can be omitted from analysis or, alternatively, interpolation of signals from a neighbouring set of channels can be utilized as a substitute channel.

The PCA function 42 can perform PCA on the measurement data 16 corresponding to the channels included in the selected zone, excluding any channels in the selected that had been identified as bad channels. The PCA function 42 can analyze the measurement data 16 characterizing the subset of the detected signals identified in the selected zone to provide a mechanism for identifying patterns in data of high dimensions and expressing that data in a manner that emphasizes the similarity and differences in the data, such as in a manner described herein. The PCA function 42 can calculate a covariance matrix for the measurement data 16 characterizing the subset of the detected signals identified in the selected zone. The PCA function 42 can also compute eigenvectors and eigenvalues of the covariance matrix by employing single variable decomposition, such as disclosed herein. The PCA function 42 can provide an orthogonal representation of the measurement data 16 characterizing the subset of the detected signals identified in the selected zone, in which the orthogonal dimensions can be sorted in a decreasing order of relevance such that a first component of the decomposition can be a dimension that carries the most information, such as described herein.

By employing such techniques, the PCA function 42 can calculate a virtual lead from the subset of channels. The virtual lead, corresponding to a single channel derived from the subset of input channels, can be utilized for further processing by the signal averager 30. The virtual lead creation resolves the issue of multiple computationally intensive procedures and creates an efficient format that can be used as evaluation criteria for future processes. The PCA function 42 can also be utilized to derive an optimized template from the selected template (e.g., automatically or manually selected). The PCA-optimized template, for example, can correspond to a P wave detection function for use by the signal averager 30. Thus, the PCA function 42 is utilized to detect the time location where the template matches the input signal. As disclosed herein, the actual averaging (via segment averaging function 50) is performed on the original input measurement data 16 (e.g., excluding bad channels) to mitigate loss of important information in the input data.

As a further example, the optimized template and the virtual lead can be provided to a cross correlation (CC) calculator 44. The CC calculator 44 can be employed to determine the strength of linear dependence between the optimized template and the virtual lead, which strength can be characterized in a CC signal. The CC calculator 44 can determine regions of interest (ROIs) that are set to maxima of the CC signal and a length of the optimized template, and provide the ROIs to a peak correlation coefficient detector 46 for each input channel.

The peak correlation coefficient detector 46 of the signal averager 30 can locate maximum correlation coefficients in the virtual lead by employing a smooth derivative from correlation coefficient data, in a manner described herein. The output of the peak correlation coefficient detector 46 and the ROIs can be provided to an amplitude comparator 48. Additionally, the amplitude comparator 48 can compare the amplitude of each ROI with the optimized template to calculate in error between the optimized template and the virtual lead ROI to determine each extraction point, such as in a manner disclosed herein. Each extraction point thus can correspond to a time-referenced location derived from the optimized template and the virtual lead.

The signal averager 30 can also include a segment averaging function 50 that can calculate an average for each respective channel over each of the ROIs provided from the amplitude comparator 48 for the respective channel. The averaging function can employ the extraction point (e.g., corresponding to a time location) to perform the averaging for corresponding segments in each respective channel. The segment averaging function 50 can also account for the number of bad channels detected by the bad channel detector 38, such as by excluding such bad channels from the averaging process. The method ensemble averages the detected regions and uses the signal quality information calculated previously to prevent averages with uninterpretable or poor signal quality regions. The output of the segment averaging function 50 can be provided as the averaged data 32 that characterizes an average signal for each of the ROIs, which can in some examples, corresponded to about 256 averaged signals (e.g., virtual leads). This averaging function thus evaluates smaller regions within a channel signal for signal quality rather than excluding the full channel from calculation based on an overall trend or small segment judgement. After the acceptable regions have been averaged, the data is then available for subsequent analysis and processing (e.g., for map creation or generating other outputs). The averaged data 32 can be stored in the memory 20 to represent average signal waveforms for each of the input channels corresponding to the measurement data 16.

The averaged data 32 can be provided to a mapping system 54 stored in the memory 20. The mapping system 54 can employ a reconstruction component 56 to convert the average data to corresponding reconstructed electrical activity of the organ under study (e.g., the patient's heart). In some examples, the reconstruction component 56 can combine the averaged data 32 with geometry data 58 that characterizes a geometry of the organ under study 10 and execute an inverse algorithm to reconstruct the electrical activity of the organ under study 10 on an envelope, such as and epicardial, an endocardial envelope or other envelope. The envelope can correspond to an anatomical surface of the organ or otherwise.

The mapping system 54 can also include a map generator 60 configured to produce corresponding map data based on reconstructed electrical activity of the organ under study 10 computed by the reconstruction component 56. The map data can be provided to the GUI 26 such that the GUI 26 can provide data sufficient cause the display 27 to output a map of the organ under study 10, such as a potential and/or an isochrone map.

Figure 2:
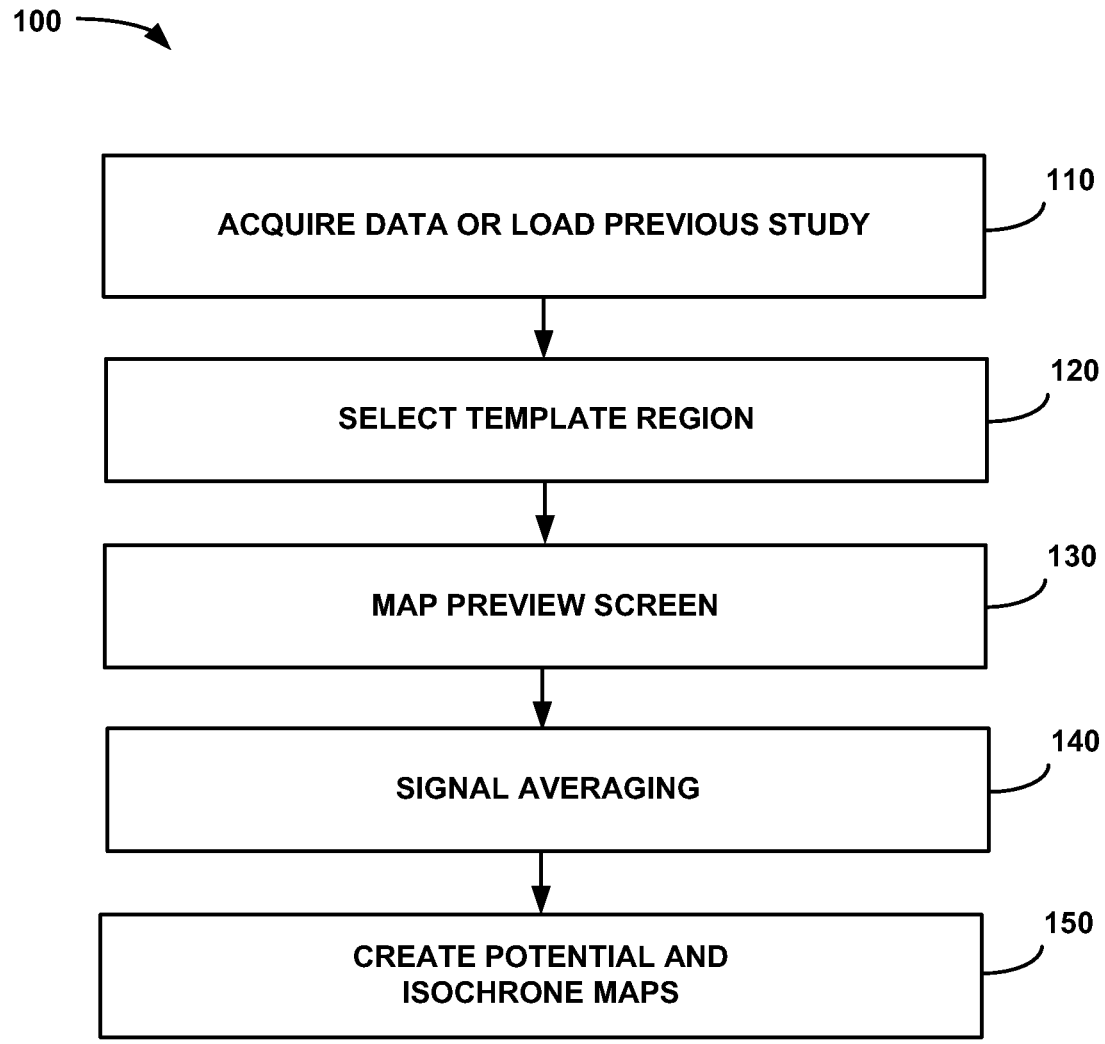
FIG. 2 illustrates a flow chart of an example user work flow for implementing signal averaging.
Figure 9:
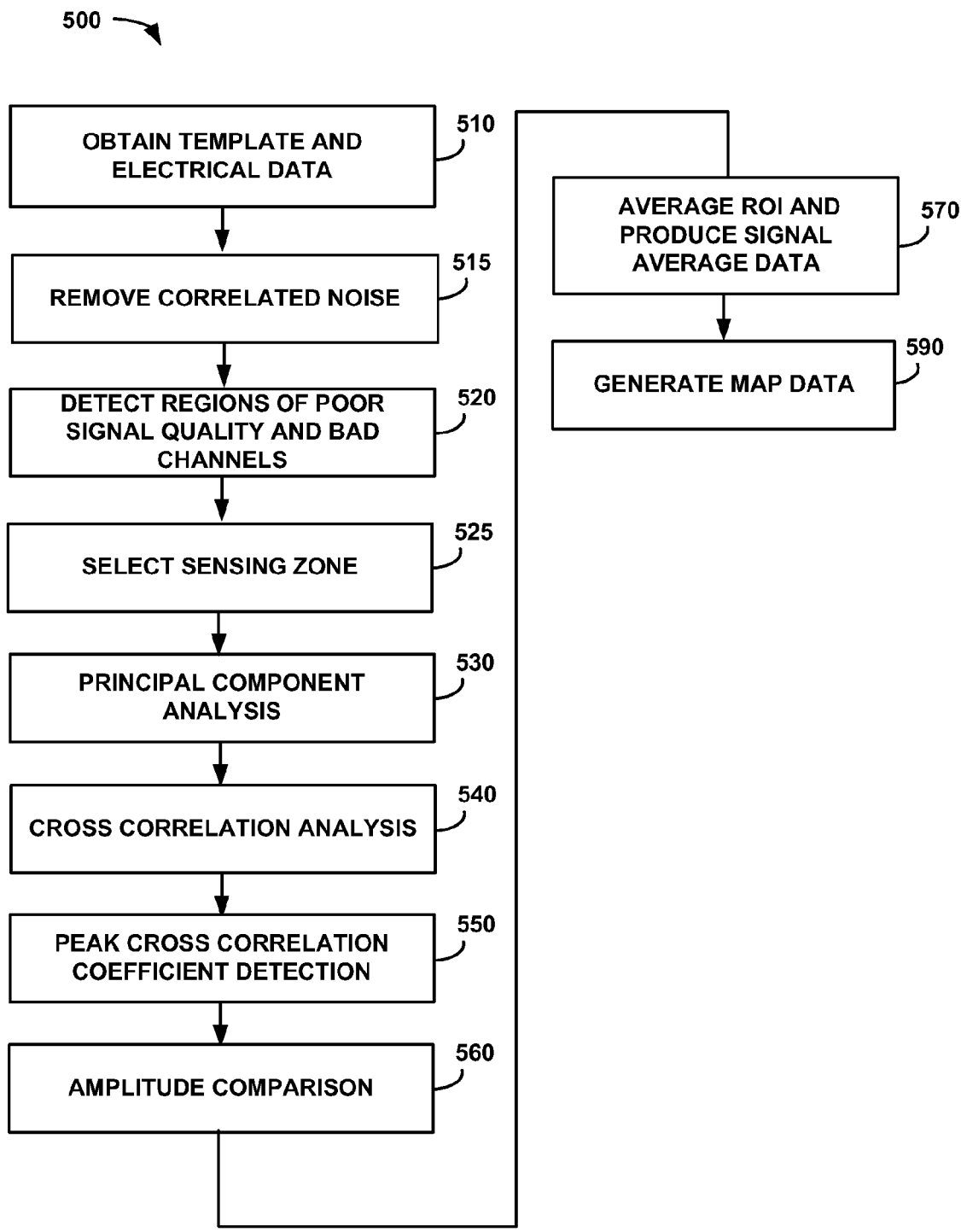
FIG. 9 illustrates a flow chart of an example method for signal averaging.

In view of the foregoing structural and functional features described above, example methods will be better appreciated with reference to FIGS. 2, 9 and 25. While, for purposes of simplicity of explanation, the example methods of FIGS. 2 9 and 25 are shown and described as executing serially, the present examples are not limited by the illustrated order, as some actions could in other examples occur in different orders and/or concurrently from that shown and described herein. Moreover, it is not necessary that all described actions be performed to implement a method. The example methods of FIGS. 2 9 and 25 can be implemented as computer-readable instructions that can be stored in a non-transitory computer readable medium such as can be computer program product. The computer readable instructions corresponding to the methods of FIGS. 2 9 and 25 can also be executed by a processor (e.g., the processing unit 22 of FIG. 2).

FIG. 2 illustrates an example method 100 of a user workflow for employing the signal averaging method. At 110, data (e.g., measurement data) can be acquired at a signal analysis system, such as the signal analysis system 18 illustrated in FIG. 1. The data can be acquired in real-time or near real-time, for example, from a plurality of sensors (e.g., the plurality of sensors 6 illustrated in FIG. 1). Alternatively or additionally, the data can be acquired earlier and loaded from a separate file (e.g., stored in memory).

Figure 3:
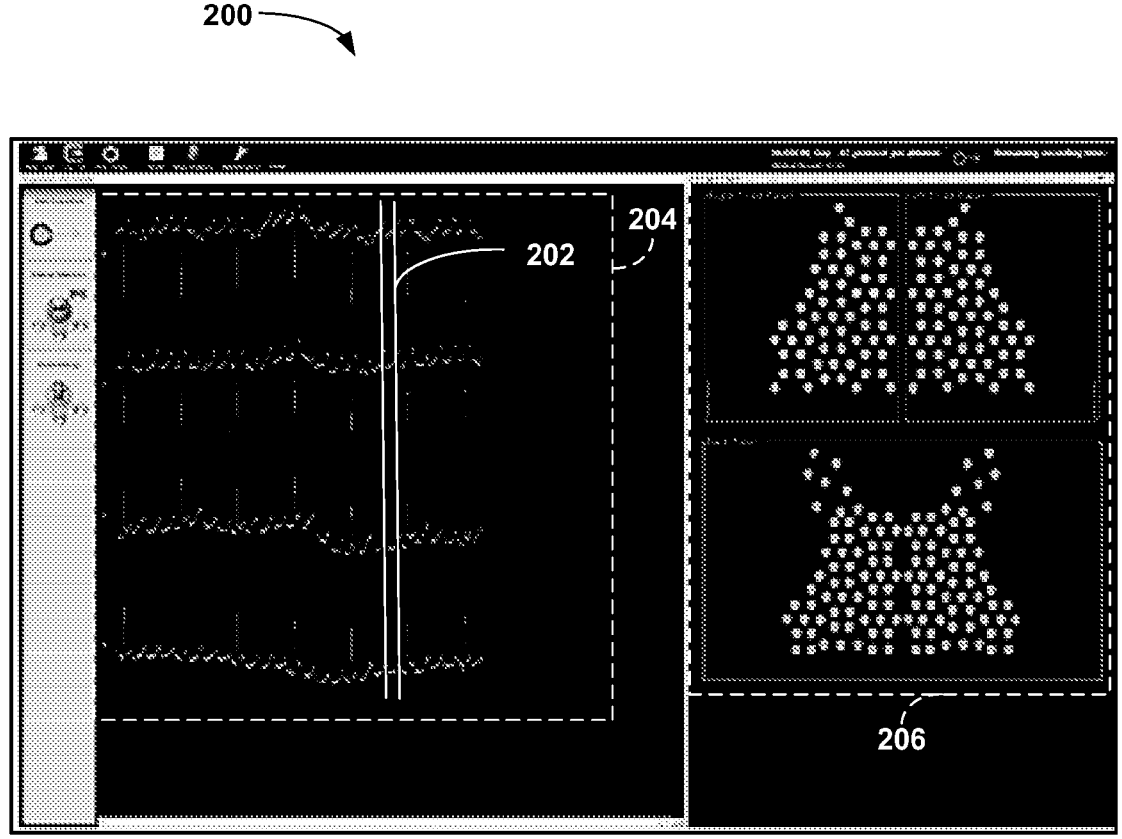
FIG. 3 illustrates an example of a template selection screen.
Figure 4:
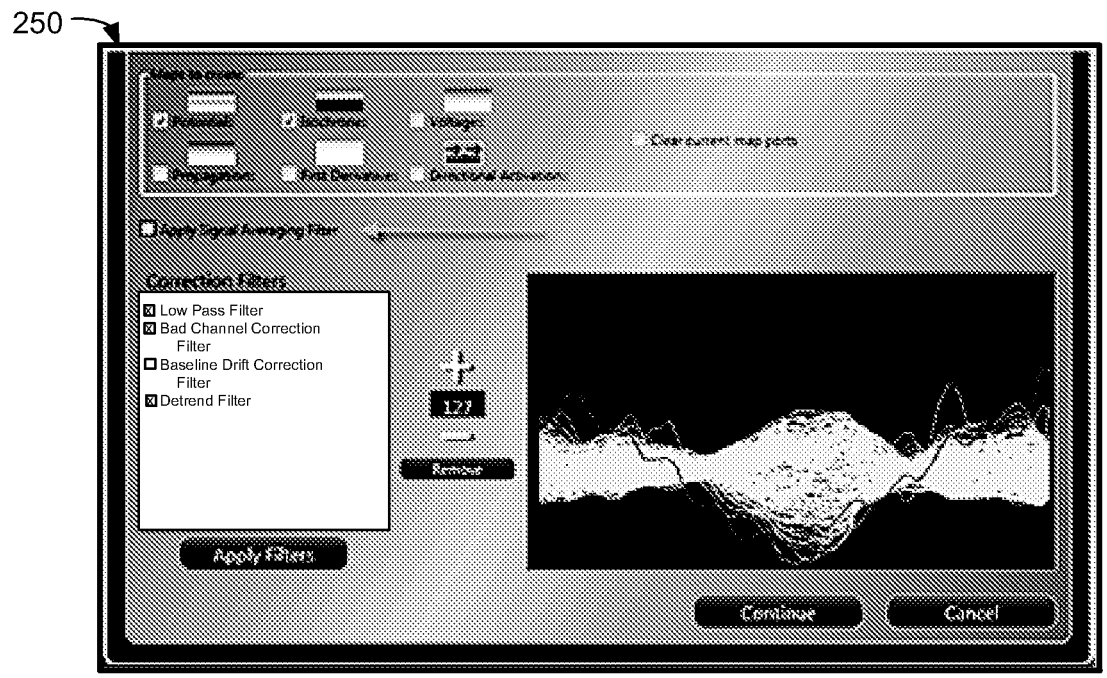
FIG. 4 illustrates an example of a map preview screen with an ability to apply a signal averaging process.
Figure 5:
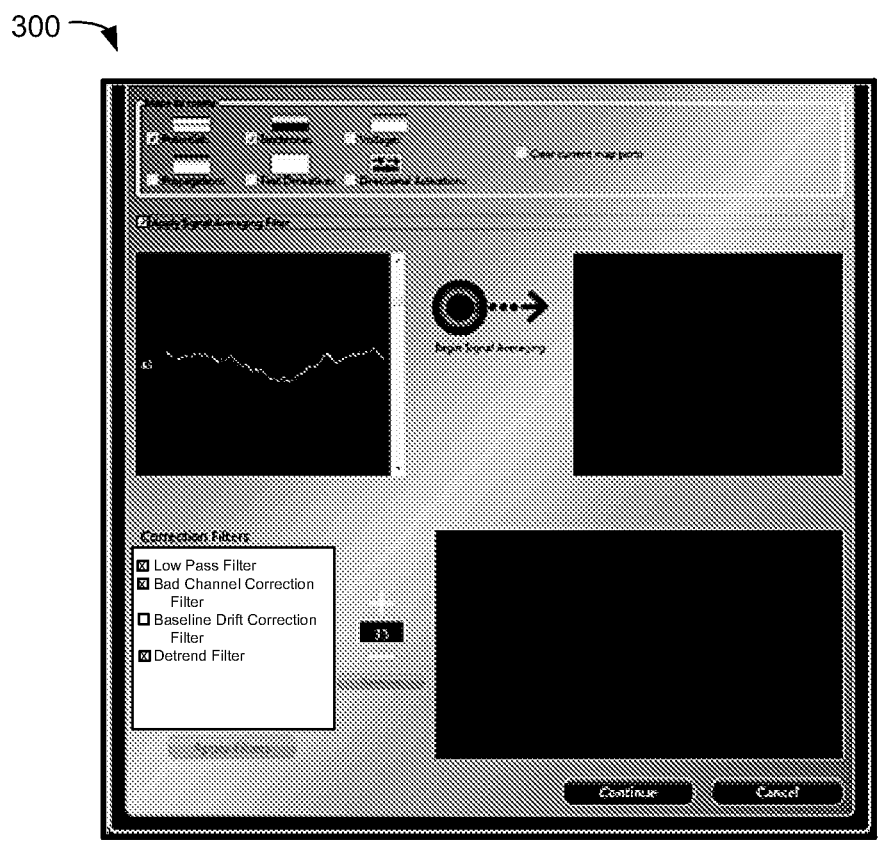
FIG. 5 illustrates an example of a pre-signal averaging screen.

At 120, the user can employ a user interface (e.g., GUI 26 illustrated in FIG. 1) to select a template region using the available selection callipers. FIG. 3 illustrates an example of a template selection screen 200 wherein calipers 202 are selected from ECG signals 204 that are provided from a sensor array 206. The user then (via the GUI) chooses to map the template region. Referring back to FIG. 2, at 130, the user can be presented with a preview of the data to be signal averaged and the ability to begin the signal averaging process. FIG. 4 illustrates an example of a map preview screen 250 with ability to apply a signal averaging process and select correction filters that can be applied to the acquired data. FIG. 5 illustrates an example of a pre-signal averaging screen 300. Referring back to FIG. 2, before the template is matched, at 140 a signal averaging process is initiated such as in response to a user input (e.g., CONTINUE GUI element in FIG. 5).

Figure 6:
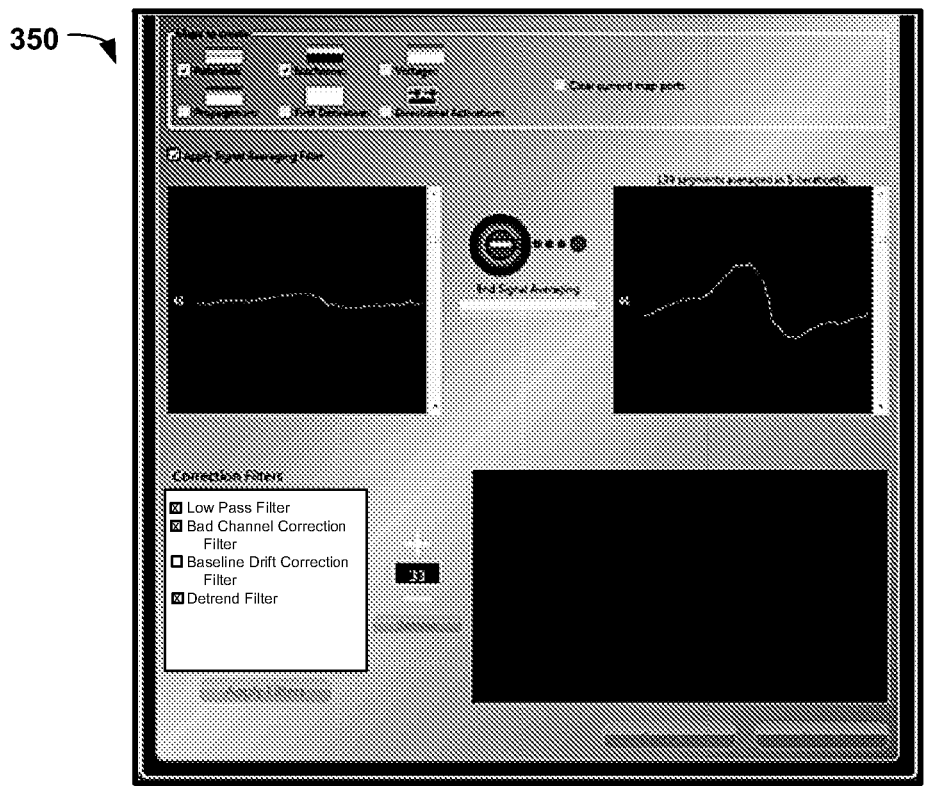
FIG. 6 illustrates an example of a signal averaging process running.

In response to initiating the signal averaging at 140, a display can show the current signal averaging results as well as the mean number of segments averaged and the iteration number. FIG. 6 illustrates an example of a signal averaging process screen 350 running. The signal averaging process can terminate (e.g., end) automatically when a user defined number of segments averaged are reached or if the process reaches the beginning of the data set. The user can also stop the process manually (e.g., in response to providing an input via a GUI, such as the GUI 26 illustrated in FIG. 1).

Figure 7:
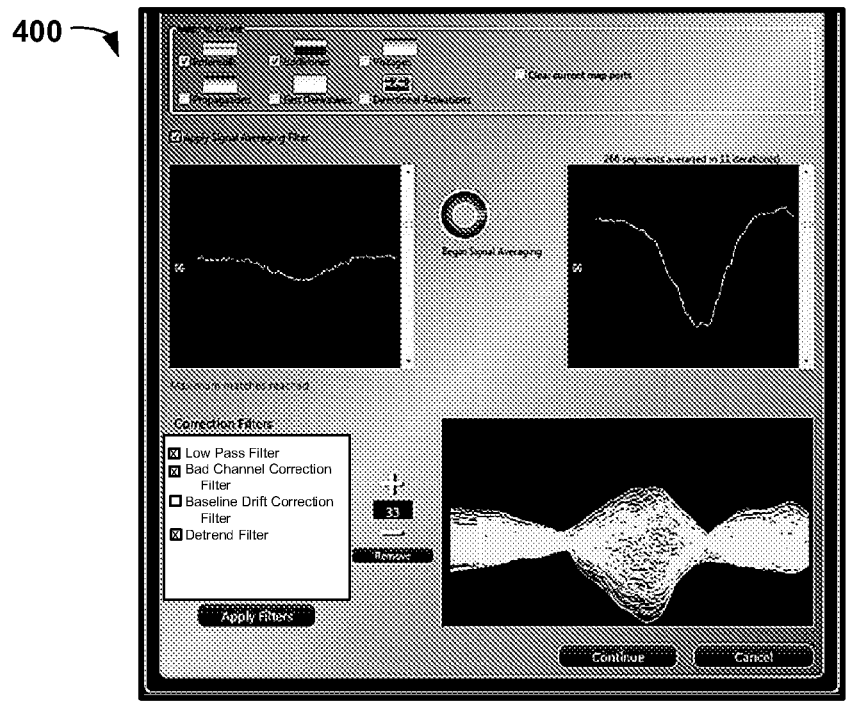
FIG. 7 illustrates an example of completed signal averaging results with a maximum number of segments averaged reached.
Figure 8:
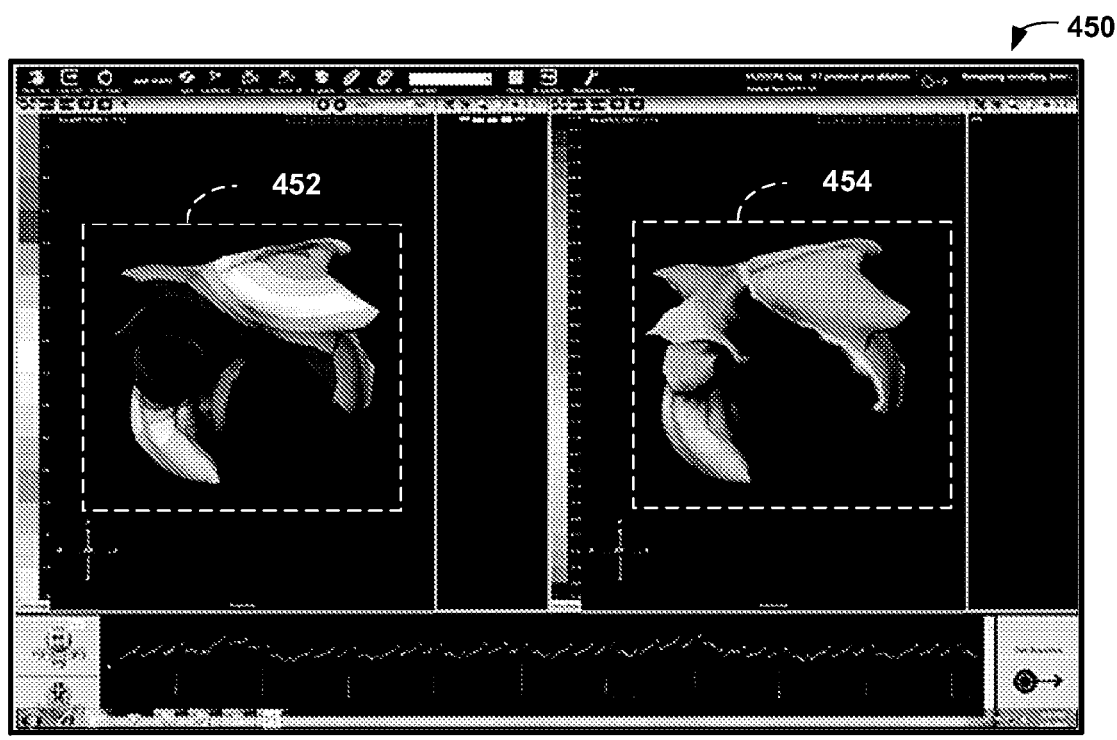
FIG. 8 illustrates an example of potential and isochrones maps created from signal averaged data.

FIG. 7 illustrates an example of a completed signal averaging results screen 400 with a predefined maximum number of segments averaged reached. Referring back to FIG. 2, upon completing the signal averaging, at 150, the user can use perform inverse solution techniques on the averaged data (e.g., the averaged data 32 illustrated in FIG. 1) to generate potential and isochrone maps. In some examples, the potential and isochrone maps can be generated, for example by the mapping system 54 illustrated in FIG. 1. FIG. 8 illustrates an example screen 450 of a potential map 452 and an isochrone map 454 that can be created from signal averaged data.

FIG. 9 illustrates an example process flow chart representing a signal averaging method 500. The method 500 could be implemented, for example, by the signal averager 30 illustrated in FIG. 1.

At 510, a template region and ECG data can be obtained, such as described with respect to FIG. 2. By way of example, the signal averaging method 500 (e.g., algorithm) can receive the following inputs: the ECG data signal, the previous number of segments averaged, the previous averaged signal, the threshold of the correlation coefficients, the number of segments to average until the process returns a value to stop averaging, the template signal, a list of bad channels, the sensing zone channels, and the rate at which the data was sampled. As an alternative or in addition to the sensing zone channels, a minimum number of channels can also be provided as an input such that the minimum number of channels can be required in order to implement the signal averaging method 500. In situations when a sensing zone is utilized, the location of the electrodes can be considered sufficient such that the minimum number of channels can be ignored or a different minimum number can be used depending on the channels in the sensing zone.

At 515, correlated noise can be removed from the input signals (e.g., by the measurement system 52 illustrated in FIG. 1). This can be performed before or after the electrical data is acquired by the method 500. The noise which the signal averaging method can efficiently remove is uncorrelated, or random. To mitigate correlated noise from entering the signal averaging process, a line filter and a low pass filter can be implemented (e.g., part of the measurement system 12 of FIG. 1) before the data was processed by the signal averager. A line filter can remove the 60 Hz (or 50 Hz for European outlets) and further harmonics of 60 Hz ambient noise from the signals. A 100 Hz Butterworth low pass filter will remove frequencies above 100 Hz, given that the frequency spectrum of ECG signals is between 0.05 Hz and 100 Hz. The 100 Hz low pass filter is a standard for United States ECG machines. Such filters can be implemented in hardware, software or a combination thereof.

As an example, for white noise, the noise level can be represented as the standard deviation, or σ (sigma). The probability of detecting a signal with an amplitude range of $\sigma_{DS}$ (DS=detected signal) is based on the input signal noise level ($\sigma_{noise}$) and the number of waveforms averaged (Nb) and can be calculated with Equation 1.

$$p(X) = 1 - \frac{\sqrt{N_b}}{\sigma_{noise}} \frac{1}{\sqrt{2\pi}} \int_{-X}^{X} \exp\left(-\frac{1}{2}\left(\frac{\sqrt{N_b}}{\sigma_{noise}} t\right)^2\right) dt. \qquad \text{Equation 1}$$

Equation 1 represents the probability of extracting a signal of certain amplitude from a signal with a certain noise level after a specified number of waveform averages. Since the signal averaging method employed by the signal averager would be applied to detect signals as low of voltage as 3 μV for PV reconnection analysis, 3 μV was the baseline signal amplitude used for analysis.

At 520, regions of poor signal quality and bad channels can be detected and stored in a memory (e.g., of the signal analysis system illustrated in FIG. 1). For example, bad channels can be detected by a bad channel detector (e.g., the bad channel detector 38 illustrated in FIG. 1). Input bad channels can be defined as channels which were missing from the CT scan, were completely saturated, or were chosen by the user (e.g., manually selected via a GUI, such as the GUI 26 illustrated in FIG. 1) as bad channels. Additionally, such detection can employ, for example, discrimination methods, such as bad channel detection and amplitude comparison, to search all channels of torso potential data (or other data) for a matching morphology of a chosen template signal within a limited threshold range. The highest quality matching regions thus can be averaged per channel and the resultant data is returned such that the detected regions of poor signal quality and/or bad channels can be ignored. The bad channel detector can utilize a predetermined temporal windowed segment of data for each iteration (e.g., about 30 seconds of data). For consecutive iterations, systems and methods can retrieve 30 seconds of data before the previous iteration.

As further example, to detect the regions of poor signal quality and/or bad channels, the bad channel detector can employ a bad channel detection algorithm. In one example the bad channel detector can identify a channel as a "bad channel" in response to determining, for example, if either all the data points in the channel are zero or 75% of the signal is deemed as of poor signal quality. For instance, the input data can be divided into segments of a plurality of data points (e.g., 2000 data points, or less if the data set contained less than 2000 data points). The bad channel detector can evaluate each windowed segment based on the variation of the baseline, amplitude changes between windows, large amplitude changes, and all zero data (no information).

For each windowed segment, the bad channel detection at 520 can calculate a baseline with a low pass filter FIR digital filter (e.g., a 0.1 Hz LPF) employing the window method. The baseline can be subtracted from the signal in order to make a comparison the signals with and without the baseline. The bad channel detection can compare each windowed segment to the previous segment for variations between the amplitude and baseline drift. The segment can be evaluated for the variation of the signal from the baseline and if the signal contained all zeros. If any of these criteria were met, the segment can be marked (e.g., bad channels) as not acceptable to average, and/or of poor quality. Segments that were not identified as bad channels can be averaged. If the channel has a predetermined amount (e.g., about 75%) or more of the total segments unacceptable, then the channel can be declared a "bad channel" and would be removed from the averaging process, resulting in zero averages for the iteration. The information about the segments' quality can be stored in memory.

At 525, a sensing zone can be selected (e.g., the zone selector 40 illustrated in FIG. 1). To select the sensing zone, the zone selector can receive study data that identifies a subset of the detected channels which can be referred to as sensing zone channels. In some examples, the sensing zone can be predefined based on a study identified in the study data (e.g., an atrial study or a ventricle study). In other examples, the sensing zone channels can vary based on the patient and/or a geometry of a sensor array (e.g., the sensor array 6 illustrated in FIG. 1). The zone selector can select a sensing zone corresponding to the sensing zone channels based on the study data. Data characterizing the sensing zone channels in the sensing zone can be provided to a PCA function (e.g., the PCA function 42 illustrated in FIG. 1).

At 530, the PCA can be performed (e.g., by the PCA function 42 of FIG. 1) such as to optimize performance and increase accuracy. The PCA can be implemented on the sensing zone channels and bad channels in the zone can be excluded. The PCA can provide a mechanism of identifying patterns in data of high dimensions and express that data in a manner to emphasize the data's similarities and differences. The PCA function could be useful, for example, when measures on a number of observed variables were obtained and it was advantageous to develop a smaller number of artificial variables that would account for most of the variance in the observed variables. The principal components can be used as predictor or criterion variables in subsequent analyses. A principal component could be defined as a linear combination of optimally-weighted observed variables.

The PCA at 530 can include calculating a covariance matrix, performing single value decomposition, forming a feature vector, and then formulating the new data set. As an example, the analysis first calculates a covariance matrix. The covariance is the measure of the strength of correlation between two or more signals with respect to each other. The principal components of the signal can be computed by determining the eigenvectors and eigenvalues of the covariance matrix by means of a single value decomposition. The first eigenvector shows the line of best fit while other eigenvectors show less important trends.

Figure 10:
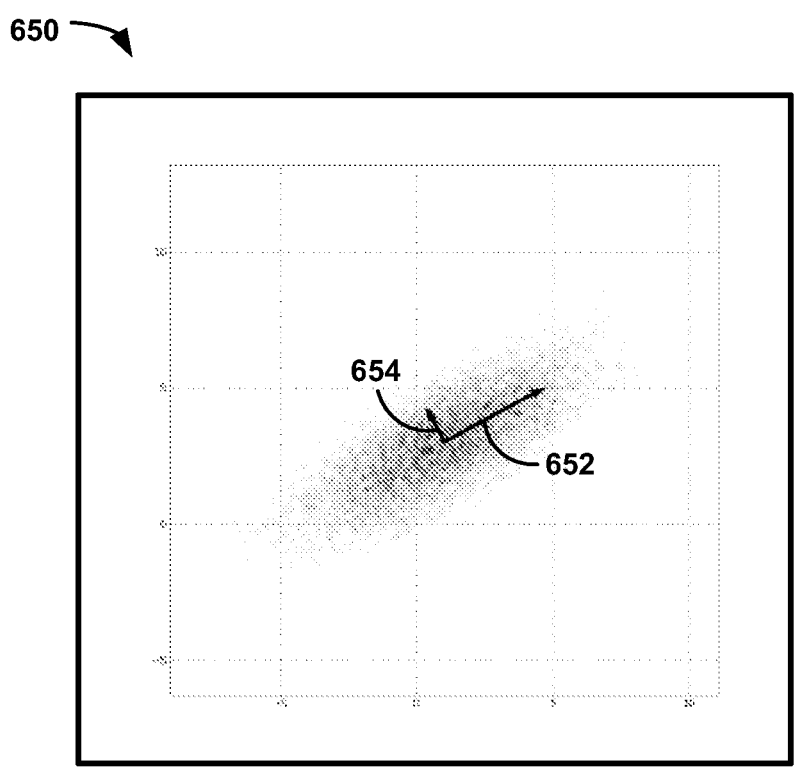
FIG. 10 illustrates an example of Eigenvalues and eigenvectors.

FIG. 10 illustrates a graph 650 demonstrates where the first and second eigenvectors 652 and 654 are plotted on a scatter plot of an example data set. The first eigenvector 652 can be varying from its direction based on the scattering of the data when the data sets contain a large number of outliers. Referring back to FIG. 9, the PCA function can calculate a virtual lead by multiplying the right singular vector by the ECG data.

The PCA function can produce an orthogonal representation of the original data in which the orthogonal dimensions can be sorted in a decreasing order of relevance. Each dimension can be obtained by a linear combination of the original data. The so-called "first component" of the decomposition can be the dimension (e.g., the linear combination of the original data) that carries the most information. As noted FIG. 10 illustrates an example of a graph 650 where the PCA function could be employed. The graph 650 of the PCA function can include an example of a "first component" 652 that is illustrated as a vector.

Referring back to FIG. 9, applied to ECG data, the first component can be determined as the linear combination that maximizes the amplitude of the signal. By way of example, let A be the matrix with the body surface ECGs. The matrix A can be an $N_s \times N_L$ matrix where $N_L$ is the number of available channels, and $N_s$ the number of samples in the record. Let T be the template manually delineated on the body surface ECGs: T was a sub-matrix of A of size $N_T \times N_L$ where $N_T$ is the number of samples of the template. The PCA can be estimated by employing Equations 3-4 which employs a svd decomposition (singular value decomposition) of the matrix T that can be expressed as:

$$T = USV^T \quad \text{Equation 2.}$$

Then $V_1$, the first column of V, is composed of the weight of the linear combination for the first component. The projection $T_M$ of the template T on the virtual lead is thus given by Equation 3:

$$T_{PCA1} = \sum_{i=1\ldots N_L} V_1(i) T_i. \quad \text{Equation 3}$$

wherein:

$T_i$ is the i-th column of T (e.g., the ECG of the Template on channel #i). $T_{PCA1}$ is of size $N_T \times 1$.

The virtual lead for the entire record can be obtained by Equation 4:

$$A_{PCA1} = \sum_{i=1\ldots N_L} V_1(i) A_i. \quad \text{Equation 4}$$

wherein:

$A_i$ is the i-th column of A (e.g., the ECG on channel #i). The size of $A_{PCA1}$ is $N_s \times 1$.

The results can provide an optimized template and a virtual lead ECG signal, each corresponding to a single channel. As noted, the graph 650 illustrated in FIG. 10 illustrates an example of Eigenvalues and eigenvectors 652 and 654.

Referring back to FIG. 9, at 540 cross correlation analysis of the acquired input signals can be performed (e.g., by the CC calculator 44 illustrated in FIG. 1). Cross correlation can be employed as a statistical method to determine the strength of linear dependence between two signals, such as in this example between the optimized template signal and the ECG virtual lead, which as explained herein can both be calculated from the PCA. The CC calculator can localize the template T (Equations 2 and 3) in the signal A by computing the CC function between the template on the virtual lead $T_{PCA1}$ and the ECG signal on the virtual lead $A_{PCA1}$ to provide a CC signal. The regions of interest (ROI) are set at the maxima of the CC signal and extend the length of the template. For example, the correlation coefficients can range from −1 to 1, with −1 representing the anti-correlation or a negative linear correlation, 0 representing no correlation, and 1 representing perfect positive correlation. Positive correlation values can be evaluated by the CC calculator. The correlation coefficient threshold can be set as a parameter that can be adjusted by the user via the GUI or automated methods can be employed. As one example, the correlation coefficient threshold can be initially set to 0.93.

At 550, peak cross correlation coefficients can be detected (e.g., by the peak correlation coefficient detector 46 illustrated in FIG. 1). For example, once the correlation coefficients were calculated for the length of the virtual lead, the peak correlation coefficient detector can determine locations of maximum correlation coefficients. To accomplish this task, for instance, a smooth derivative can be computed for the correlation coefficient data, with the x-coordinates representing the location in time that the event occurred and with the y-coordinates representing the correlation coefficients. The location in time where the derivative crosses zero (e.g., when polarity of the derivative changes) represents a peak. A check can be performed for a crossing where the slope changes from positive to negative to preclude local maxima. The peak values can be stored in memory as a potential starting array point, and/or "extraction points" for signal averaging. Once this process is completed for the length of the virtual lead, the correlation coefficient values at these potential locations can be compared to a user defined (programmable) correlation threshold. As an example, the threshold can be set at 0.90.

At 560, an amplitude comparison can be implemented (e.g., by the amplitude comparator 48 illustrated in FIG. 1). The amplitude comparison can compare the amplitude of each determined ROI relative to the PCA optimized template signal. The amplitude comparison can calculate an error between the template and the virtual lead ROI for each extraction point. A unique Gaussian (or other) curve fitting technique can be employed to fit the distribution of the error values. If a single curve was detected, the error limit can be determined by adding 2.5 times the standard deviation to the peak value. If more than one curve is detected, the amplitude comparator can calculate the intersection point between the Gaussian curves. If this intersection point is determined to be of a size great enough to demonstrate a difference in morphology between signals, the amplitude comparator can calculate the error limit from this point between the curves. However, if the curves are within a small range of each other, the amplitude comparator can treat the curves as one curve and the method for a determining the error limit from a single curve can be applied. The ROIs can be compared to the calculated error limit and removed if outside the error range.

At 570, the ROI can be averaged (e.g., by the segment averaging function 50 illustrated in FIG. 1) to produce averaged data (e.g., the averaged data 32 illustrated in FIG. 1). By way of example, since the bad channel detection can remove certain channels and provide a method for discriminating against poor signal quality regions within the signal, each channel can result in a different number of averages per iteration. Given this, a variable can be passed as one of the output parameters that tracks the cumulative sum of the averages on each channel. The sum of the segments averaged per channel can be used for consecutive iterations of signal averaging.

As an output from the bad channel detection (at 520), a decision variable that represents information as to the acceptability of the sub-regions within the iteration can be provided. Each extraction point can correspond to a time referenced location that can be compared to the respective decision variable that represented the location (e.g., a time-referenced location) within the full signal to determine if the region is acceptable. Once the extraction points had been deemed adequate for averaging, the segment averaging function at 570 can ensemble average a region, starting with the extraction point and extending the length of the template. The averaging process can be carried out for all ROIs specific to that channel. For instance, each channel may have different ROIs that are to be averaged by the averaging function 570. The segment averaging thus can be implemented for each channel individually. During this process, the DC offset can also be removed, thereby making the noise zero-mean. Due to the differing number of averages per channel, the mean value of the number of segments averaged per channel corresponds to the overall output for the number of segments averaged to the user.

In the foregoing example, it was assumed that the P-waves and T-waves of the signal to be averaged would be significantly different from one another. However, if there is a case where the P-waves and T-waves become similar in amplitude and duration, the amplitude comparison method was designed to limit the number of false detections. In such a situation, the amplitude comparator can generate a distribution based on the difference between each ROI and the template signal. The distribution can reveal that there could be two or more Gaussian curves fitted. Each curve would represent a region of specific error related a different waveform. If the regions, or curves, are within a predetermined value of (e.g., about 2.5) standard deviations, then the error difference can be considered too small and all of the ROIs are selected for averaging. However, if the curves are greater than the predetermined standard deviations, the ROIs that have an error less than the intersecting point between the curves are selected for averaging. The amplitude comparator can include error comparison that can prevent the number of false detections by comparing the amplitude of the ROIs to be averaged.

This amplitude comparison at 560 thus allows for an automated method that can create distributions and determine an upper limit to differentiate signal morphologies. Additionally, the amplitude comparison can be programmed as to be used only if the previous averaging criteria (e.g., for a preceding cycle) were met.

At 590, map data can be generated based on the averaged data provided at 570 (e.g., by the mapping system 54 of FIG. 1). For example, an inverse method can be performed on the averaged data generate electrophysiological data by combining body surface electrical measurements with patient geometry information through an inverse method programmed to reconstruct the electrical activity for a predetermined surface region of the patient's region of interest (e.g., heart or brain). For example, the map can represent electrical activity for each of a plurality of points on a cardiac envelope (e.g., in the form of potential and isochrone maps) concurrently as a function of time, such as an epicardial surface, endocardial surface or other envelope. Examples of inverse algorithms that can be utilized in the system 10 are disclosed in U.S. Pat. Nos. 7,983,743 and 6,772,004, which are incorporated herein by reference. The output maps can be displayed to the user via the GUI (e.g., the GUI 26 illustrated in FIG. 1).

Employment of the methods and systems here can provide relatively accurate results. By way of example, to measure the accuracy of detection, ten signals of 75,000 data points over 256 channels were used from the data cases. For each signal, a P-wave template can be chosen and the template was signal averaged. The output plots showed the locations where the template was detected on a specified channel. For instance, in the referenced test scenario, since the maximum number of segments was defined at 250 averaged, to detect a 3 µV signal greater than 75% of the time, the noise level can be below 20 µV. If the noise level is below 15 µV, the 3 µV signal can be detected 89% of the time and if the noise level is below 10 µV the signal can be detected 98% of the time with 250 averages. An example of the results, demonstrating statistical analysis of probability to detect an event, are shown in Table 1.

TABLE 1

| | | Noise Level (sigma) (V) | | | | | | | | | |
|---|---|---|---|---|---|---|---|---|---|---|---|
| | | 1.00E−03 | 5.00E−04 | 1.00E−04 | 5.00E−05 | 3.00E−05 | 2.00E−05 | 1.50E−05 | 1.00E−05 | 3.00E−06 | 1.00E−06 | 1.00E−07 |
| Number | 5 | 0.00268 | 0.00535 | 0.02676 | 0.05348 | 0.08902 | 0.13319 | 0.17694 | 0.26269 | 0.73645 | 0.99920 | 1.00000 |
| of | 10 | 0.00378 | 0.00757 | 0.03783 | 0.07558 | 0.12563 | 0.18748 | 0.24817 | 0.36475 | 0.88616 | 1.00000 | 1.00000 |
| Segments | 25 | 0.00598 | 0.01197 | 0.05979 | 0.11924 | 0.19741 | 0.29234 | 0.38293 | 0.54675 | 0.98758 | 1.00000 | 1.00000 |
| Averaged | 50 | 0.00846 | 0.01692 | 0.08447 | 0.16800 | 0.27633 | 0.40412 | 0.52050 | 0.71116 | 0.99959 | 1.00000 | 1.00000 |
| | 75 | 0.01036 | 0.02073 | 0.10336 | 0.20499 | 0.33500 | 0.48400 | 0.61353 | 0.80607 | 0.99999 | 1.00000 | 1.00000 |
| | 100 | 0.01197 | 0.02393 | 0.11924 | 0.23583 | 0.38293 | 0.54675 | 0.68269 | 0.86639 | 1.00000 | 1.00000 | 1.00000 |
| | 125 | 0.01338 | 0.02676 | 0.13319 | 0.26269 | 0.42385 | 0.59827 | 0.73645 | 0.90647 | 1.00000 | 1.00000 | 1.00000 |
| | 150 | 0.01466 | 0.02931 | 0.14576 | 0.28670 | 0.45971 | 0.64168 | 0.77933 | 0.93381 | 1.00000 | 1.00000 | 1.00000 |
| | 200 | 0.01692 | 0.03384 | 0.16800 | 0.32863 | 0.52050 | 0.71116 | 0.84270 | 0.96611 | 1.00000 | 1.00000 | 1.00000 |
| | 225 | 0.01795 | 0.03589 | 0.17802 | 0.34729 | 0.54675 | 0.73942 | 0.86639 | 0.97555 | 1.00000 | 1.00000 | 1.00000 |
| | 250 | 0.01892 | 0.03783 | 0.18748 | 0.36475 | 0.57081 | 0.76432 | 0.88616 | 0.98230 | 1.00000 | 1.00000 | 1.00000 |
| | 275 | 0.01985 | 0.03968 | 0.19645 | 0.38116 | 0.59299 | 0.78641 | 0.90275 | 0.98714 | 1.00000 | 1.00000 | 1.00000 |
| | 300 | 0.02073 | 0.04144 | 0.20499 | 0.39667 | 0.61353 | 0.80607 | 0.91674 | 0.99063 | 1.00000 | 1.00000 | 1.00000 |
| | 400 | 0.02393 | 0.04784 | 0.23583 | 0.45150 | 0.68269 | 0.86639 | 0.95450 | 0.99730 | 1.00000 | 1.00000 | 1.00000 |
| | 600 | 0.02931 | 0.05858 | 0.28670 | 0.53757 | 0.77933 | 0.93381 | 0.98570 | 0.99976 | 1.00000 | 1.00000 | 1.00000 |
| | 1000 | 0.03783 | 0.07558 | 0.36475 | 0.65722 | 0.88616 | 0.98230 | 0.99843 | 1.00000 | 1.00000 | 1.00000 | 1.00000 |

Figure 11:
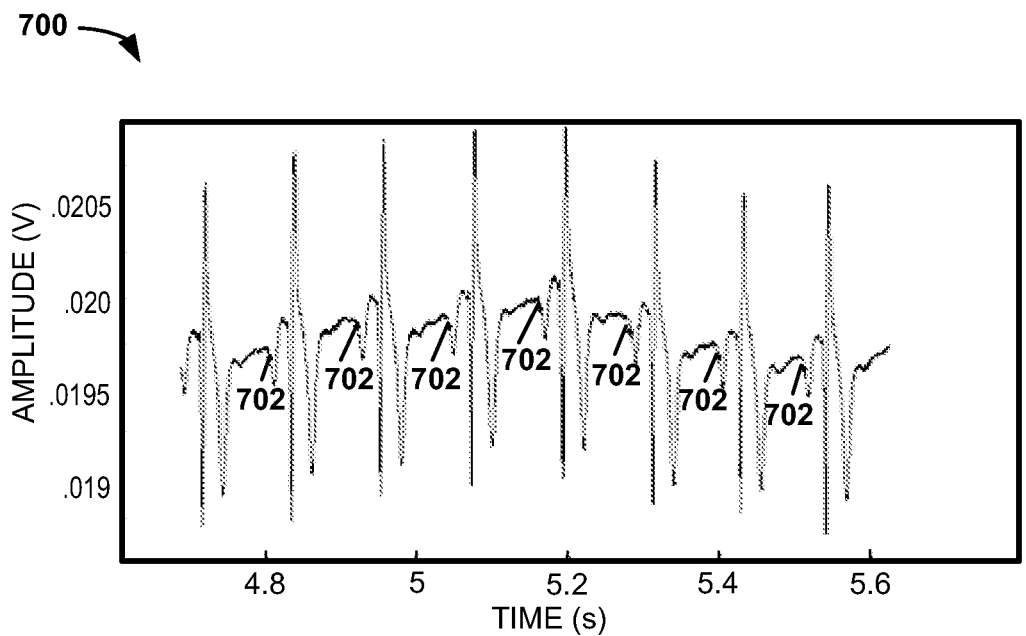
FIG. 11 illustrates an example of P-wave accuracy test results.
Figure 12:
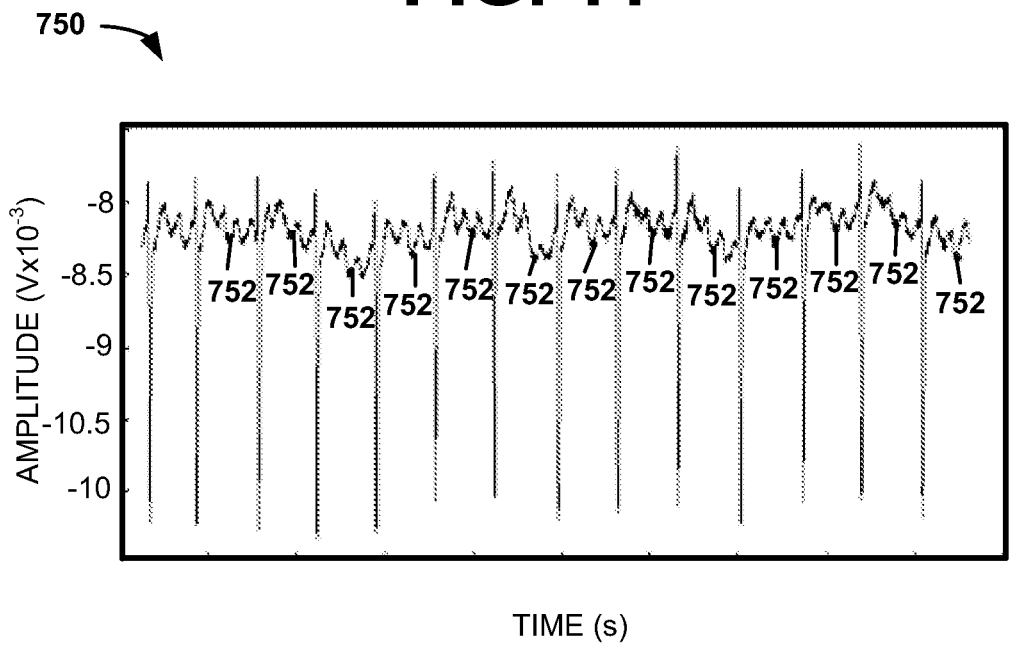
FIG. 12 illustrates another example of P-wave accuracy test results.

FIGS. 11 and 12 illustrate the P-wave accuracy results 700 and 750. It can be seen for these two examples 700 and 750 that the P-wave template was detected. FIG. 11 illustrates an example 700 of a P-wave accuracy test results, wherein dots 702 mark where a template was detected. FIG. 12 illustrates an example of another P-wave accuracy test results 750, wherein dots 752 mark where a template was detected. Some results demonstrated that T-waves were detected as P-waves when the T-wave was similar in amplitude and duration as the P-wave which was against the assumptions. The averaging method employed herein can demonstrate about 99.873% accuracy or greater.

Figure 13:
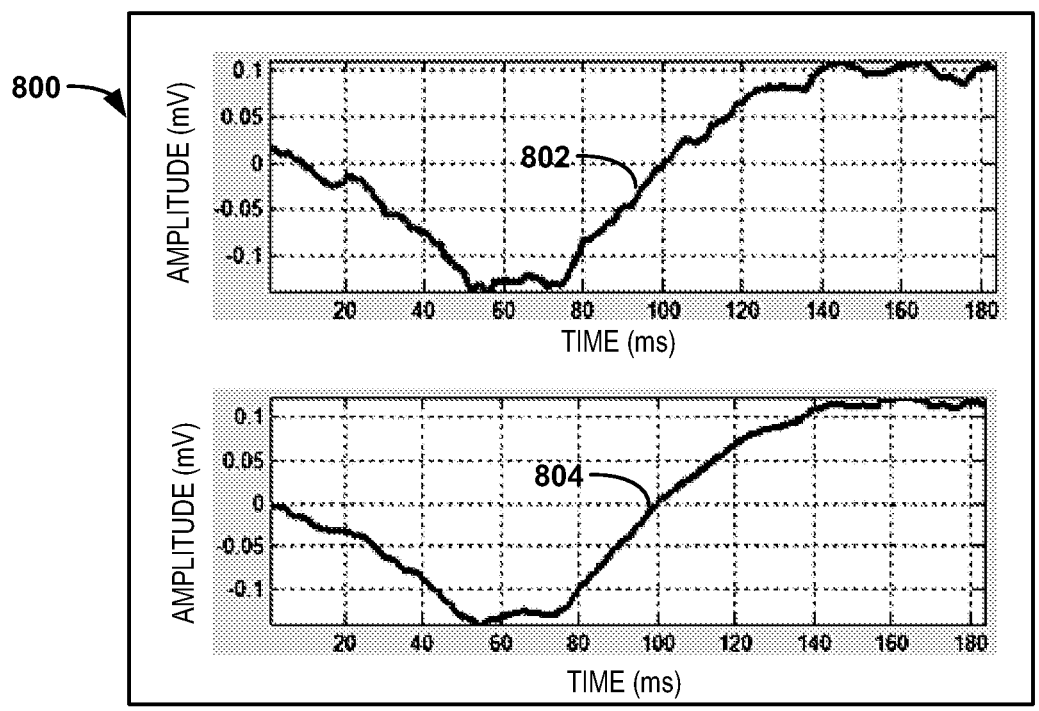
FIG. 13 illustrates an example of a template versus averaged signal comparison.
Figure 14:
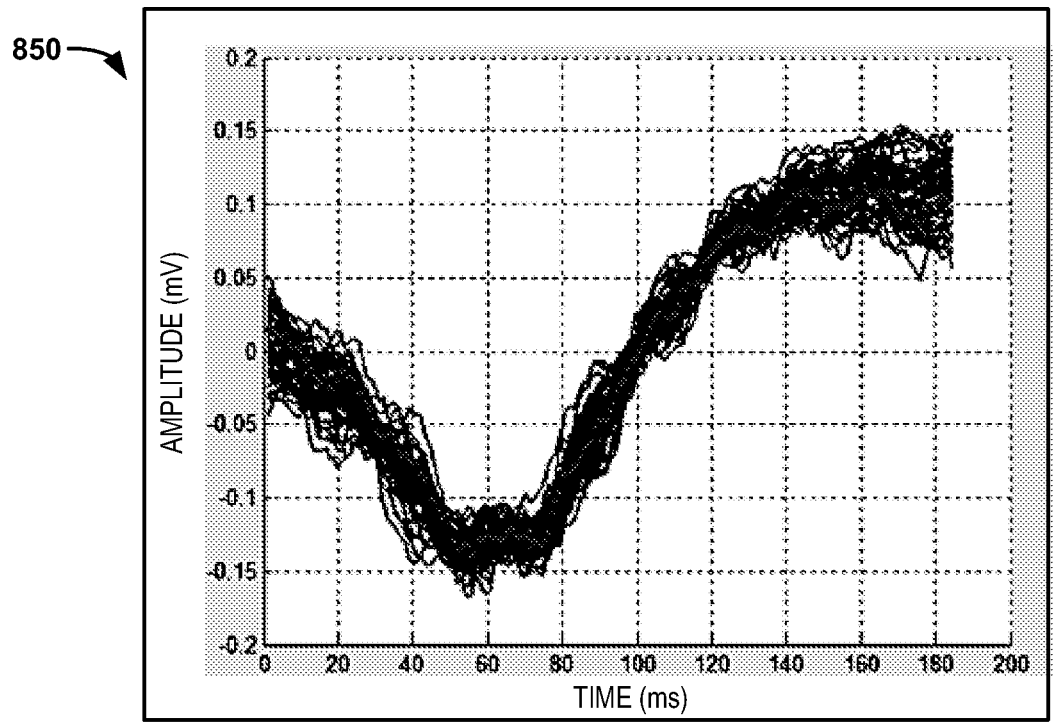
FIG. 14 illustrates an example of a composite plot of all regions of interest detected to be averaged.
Figure 15:
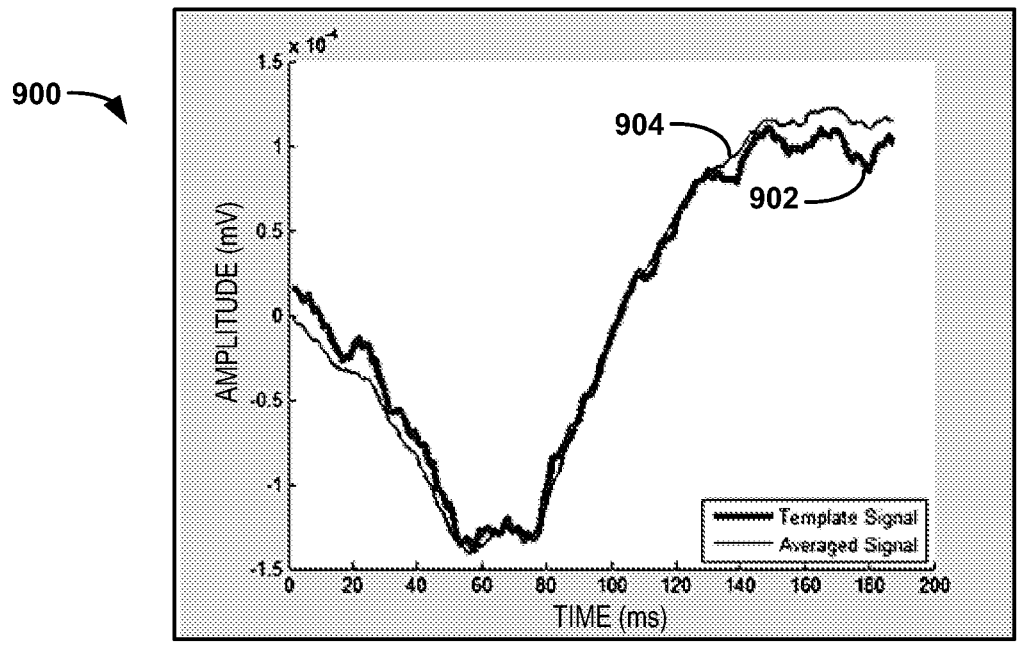
FIG. 15 illustrates an example of a template and averaged signal comparison.
Figure 16:
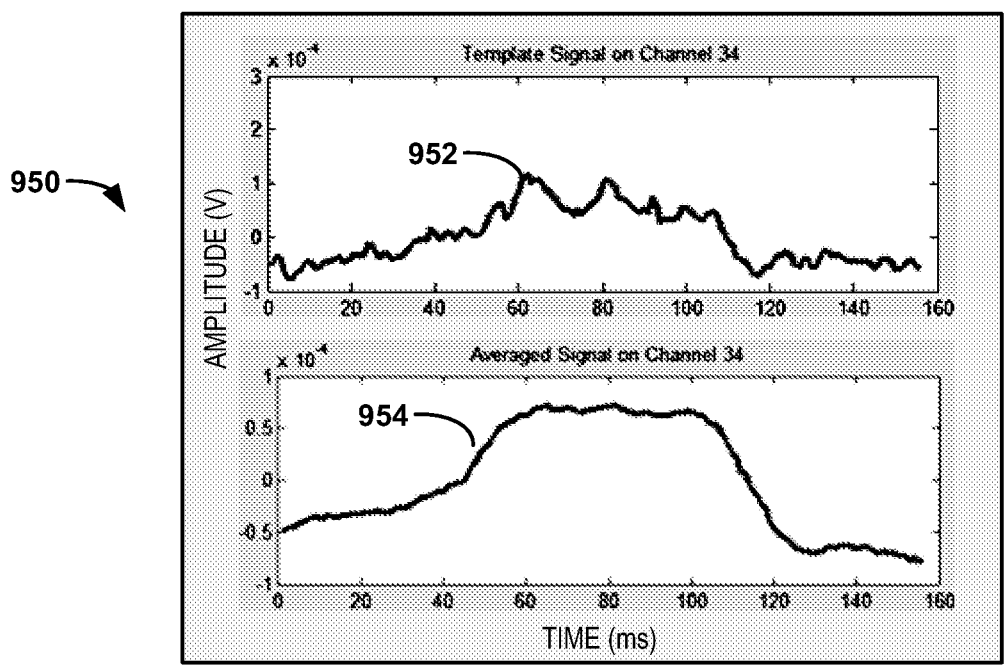
FIG. 16 illustrates an example of template versus averaged signal comparison.
Figure 17:
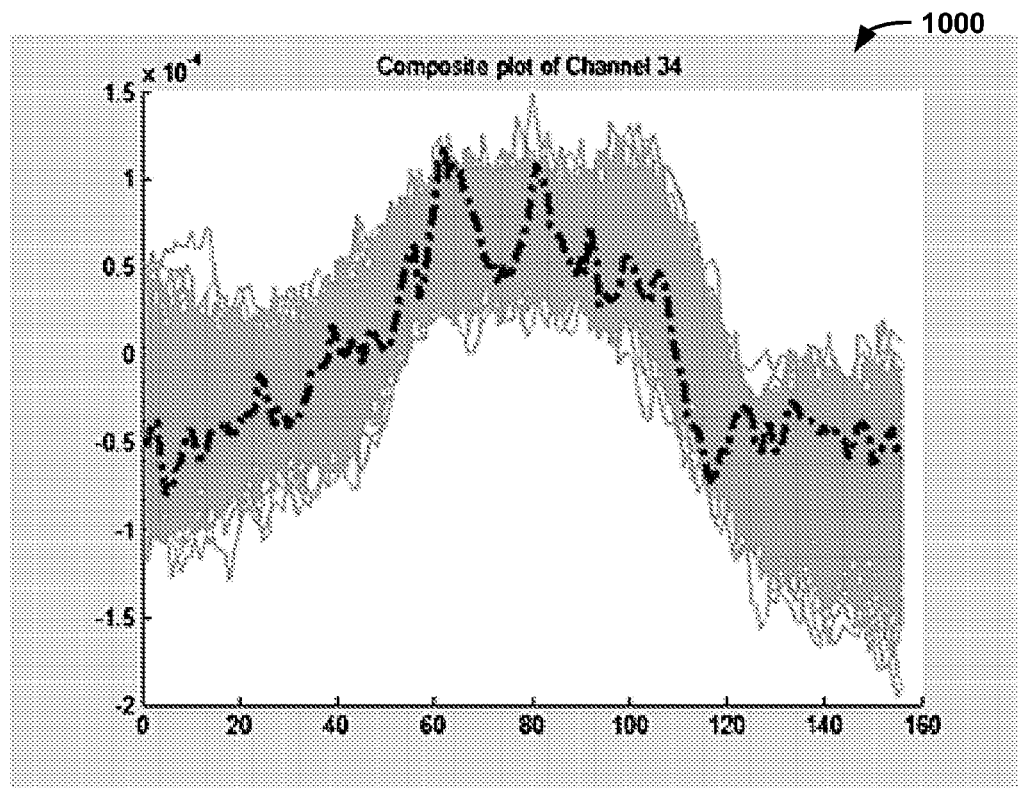
FIG. 17 illustrates an example of a composite plot of all regions of interest detected to be averaged.
Figure 18:
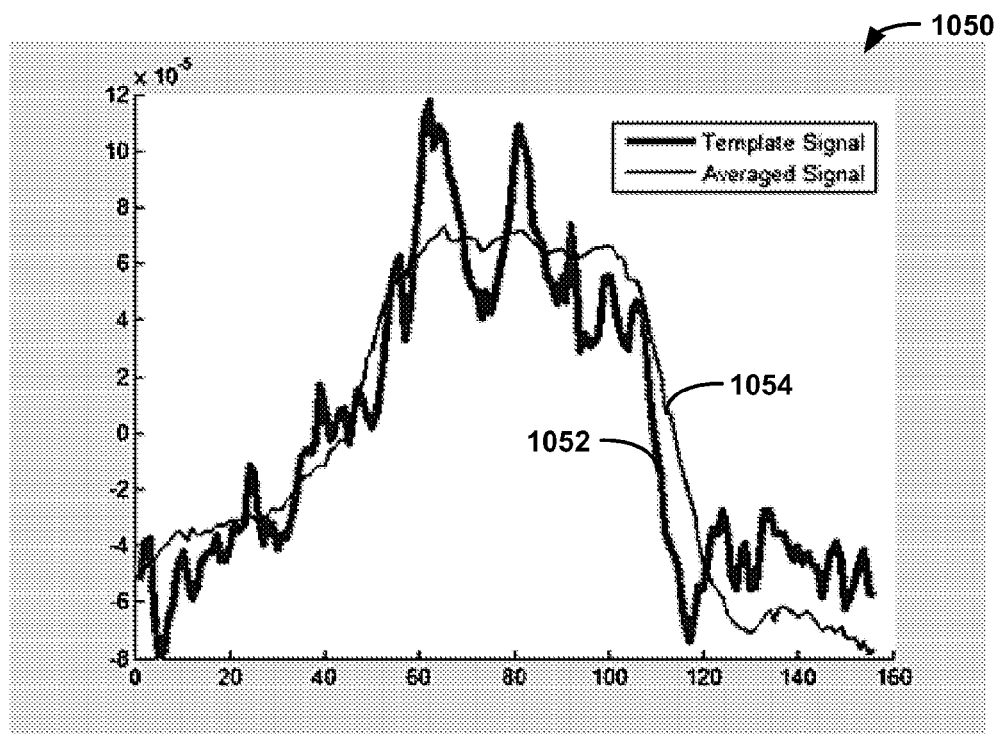
FIG. 18 illustrates an example of a template and averaged signal comparison.
Figure 19:
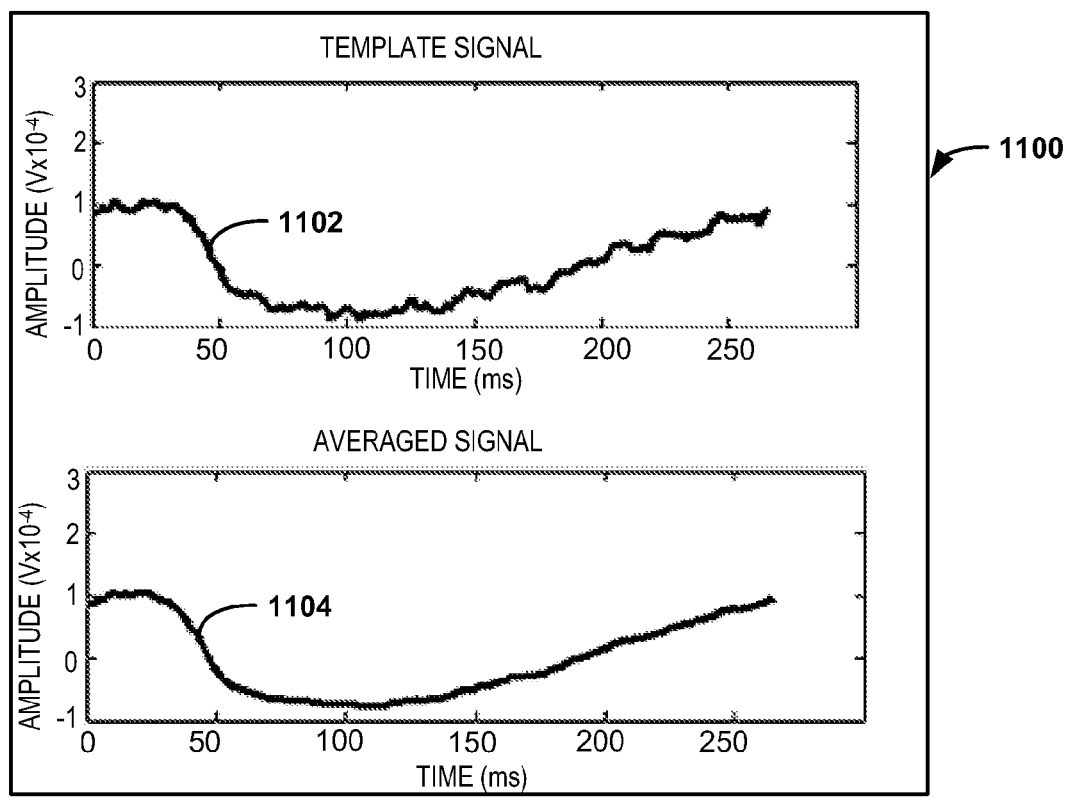
FIG. 19 illustrates an example of a template versus averaged signal comparison.
Figure 20:
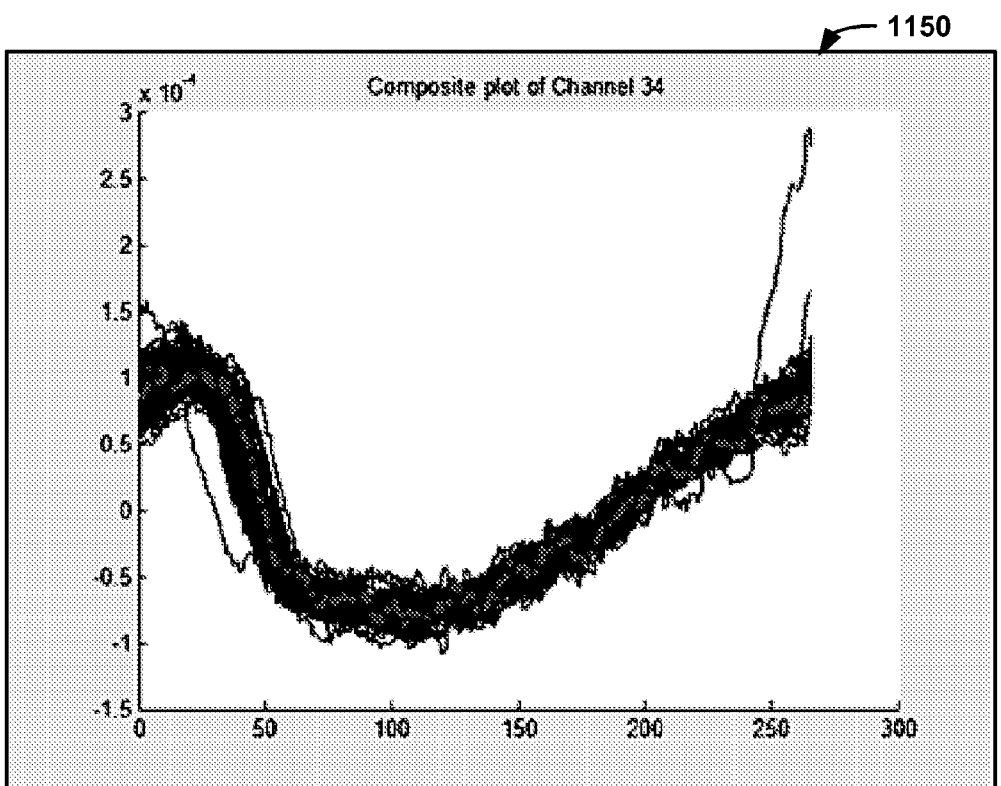
FIG. 20 illustrates an example of a composite plot of all regions of interest detected to be averaged.
Figure 21:
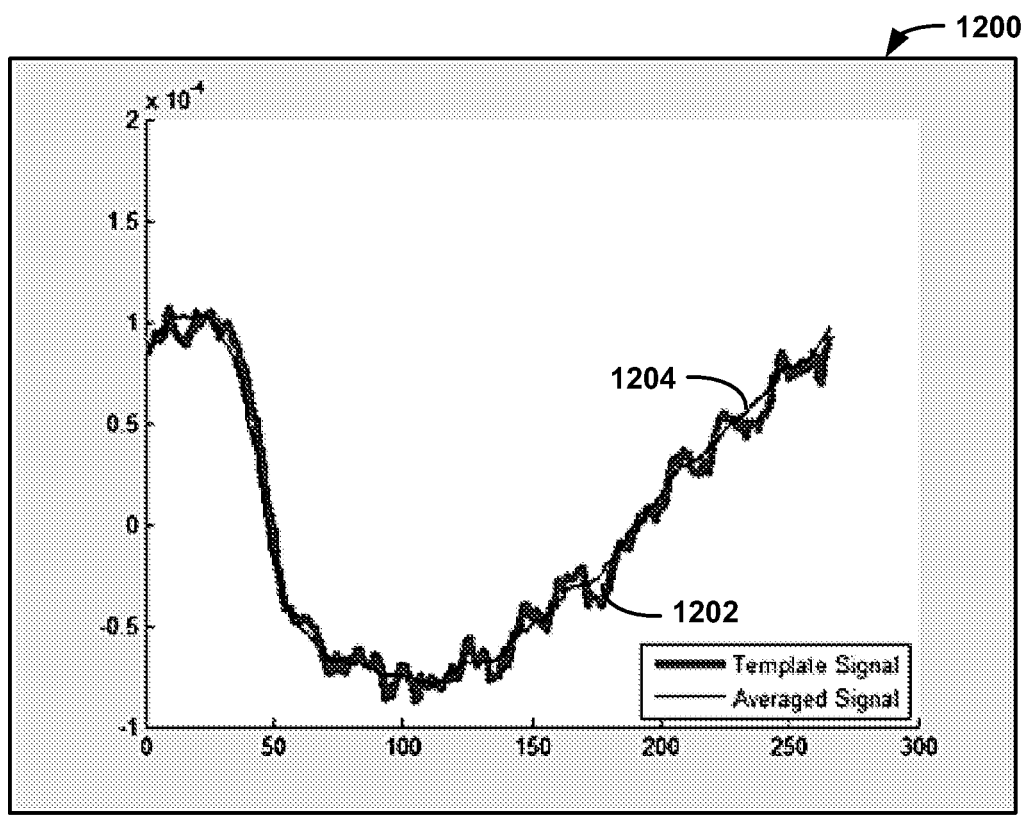
FIG. 21 illustrates an example of a template and averaged signal comparison.

FIG. 13 illustrates an example graph 800 demonstrating a first case example template 802 relative an averaged signal 804. FIG. 14 illustrates an example 850 of composite plot (for the first case) of all regions of interest detected to be averaged with DC offset removed. FIG. 15 illustrates an example 900 of the first case template 902 and an averaged signal 904 comparison. FIG. 16 illustrates an example 950 of a second case template 952 versus an averaged signal 954 comparison. FIG. 17 illustrates an example 1000 of a composite plot of all regions of interest detected to be averaged for the second case. FIG. 18 illustrates an example 1050 of the second case template 1052 and an averaged signal comparison 1054. FIG. 19 illustrates an example 1100 of a third case template 1102 versus averaged signal 1104 comparison. FIG. 20 illustrates an example 1150 of a composite plot of all regions of interest detected to be averaged for the third case. FIG. 21 illustrates an example 1200 of template signal 1202 and an averaged signal 1204 comparison for the third case.

Figure 22:
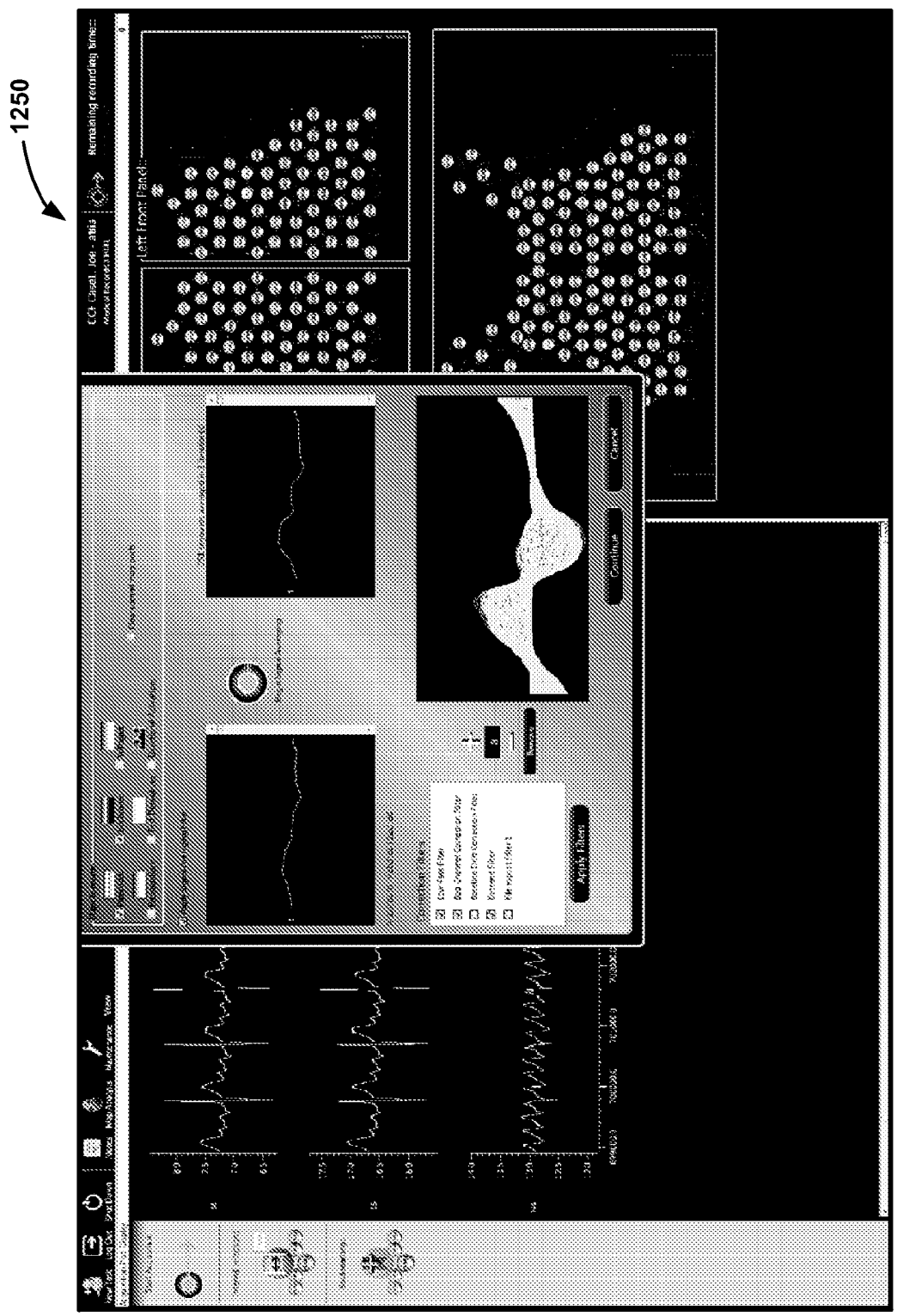
FIG. 22 illustrates an example of signal averaging results from a test case, Channel 1.

FIG. 22 illustrates an example screen 1250 depicting a GUI that can be utilized to show signal averaging results for a given channel from a sample test case. The signal averaging systems and methods disclosed herein mitigate reduce the effects of uncorrelated noise within the frequency spectrum of an ECG signal and detect low voltage signals. These systems and methods can allow for further analysis using an analysis system such as an ECGI system or other system configured to analyze detected biological signals.

In view of the foregoing, in addition to improving signal quality, the methods described herein have the unique advantage of accentuating and bringing out small, but highly key signals that are of diagnostic importance. Some examples of clinical applications that can capitalize on this approach are the following: potential-based electrocardiography calculations and detection of pulmonary vein reconnection.

Additionally, the signal averaging systems and methods disclosed herein can be combined with other analysis and signal processing techniques such as the following: automated detection of poor signal quality regions and channels, a principal component analysis, and a Gaussian curve fitting amplitude detection. The algorithm can employ the calculated signal quality information to prevent averaging of poor signal quality regions. The various features of the algorithm allow for template detection within signals with complex morphological features and cycle lengths as well as prevent false detections, which makes the method unique. The algorithm's results demonstrated that it has the capability to remove uncorrelated noise from a template signal as well as detect low voltage signals (as low as 3 µV). Overall, the advanced signal averaging can produce high quality signals to aid in innovative diagnostic techniques.

By way of example, since the demonstration that pulmonary vein (PV) ectopic activity is a main trigger of paroxysmal atrial fibrillation (AF), radiofrequency ablation (RF) of this arrhythmia has become an increasingly popular procedure in many electrophysiology laboratories. Traditionally, RF-based PVI uses a 'point-by-point' ablation technique, which makes it difficult to create continuous ablation lines and allows conduction gaps to develop which may facilitate recurrence of the arrhythmia. Either by the reduction in swelling or incomplete ablation procedures, the possibility of electrical channels reforming post-ablation impede the success of the procedure. The goal is to be able to use noninvasive electrocardiographic mapping (ECM) to identify pulmonary vein reconnection as a tool for predicting recurrence of atrial fibrillation (AF) after pulmonary vein isolation.

It can be demonstrated that the p-wave duration and area under the curve (AUC) decrease in patients post PVI whereas patients with reconnected PVs exhibit increased p-wave durations and AUC. Methods to investigate the electrograms near the PVs and carina of ipsalateral veins pre and post procedure would need to detect signals of amplitude near 2-4 µV. Given that the tissue has been ablated and is scarred, detection of these low voltage signals would be difficult when the acquisition noise levels are high (e.g., noise levels 2-5 times the amplitude of the signal). The proposed signal averaging system and method can be used for post-acquisition signal processing, to improve signal quality and allow for the detection of these low voltage signals.

As disclosed herein, the method can include a template detection process that is not dependent on pre-specified complex intervals and complex amplitudes assuming that the cycle lengths would remain constant during the detection process. The approach herein can employ an efficient comparison method to ensure that the detected regions are within the detection specification. The method can also utilize a signal averaging technique which can discriminate regions of poor signal quality and can efficiently average signals over multiple channels. The system and method provides a time-shifted cross correlation detection with the signal averaging process.

The proposed systems and methods thus can accurately detect a template signal within a large data set that can have multiple channels and improve the signal strength of the template (e.g., improves the signal-to-noise ratio gain by the square root of the number of measurements) by averaging the detected regions of the signal for each input channel.

Figure 23:
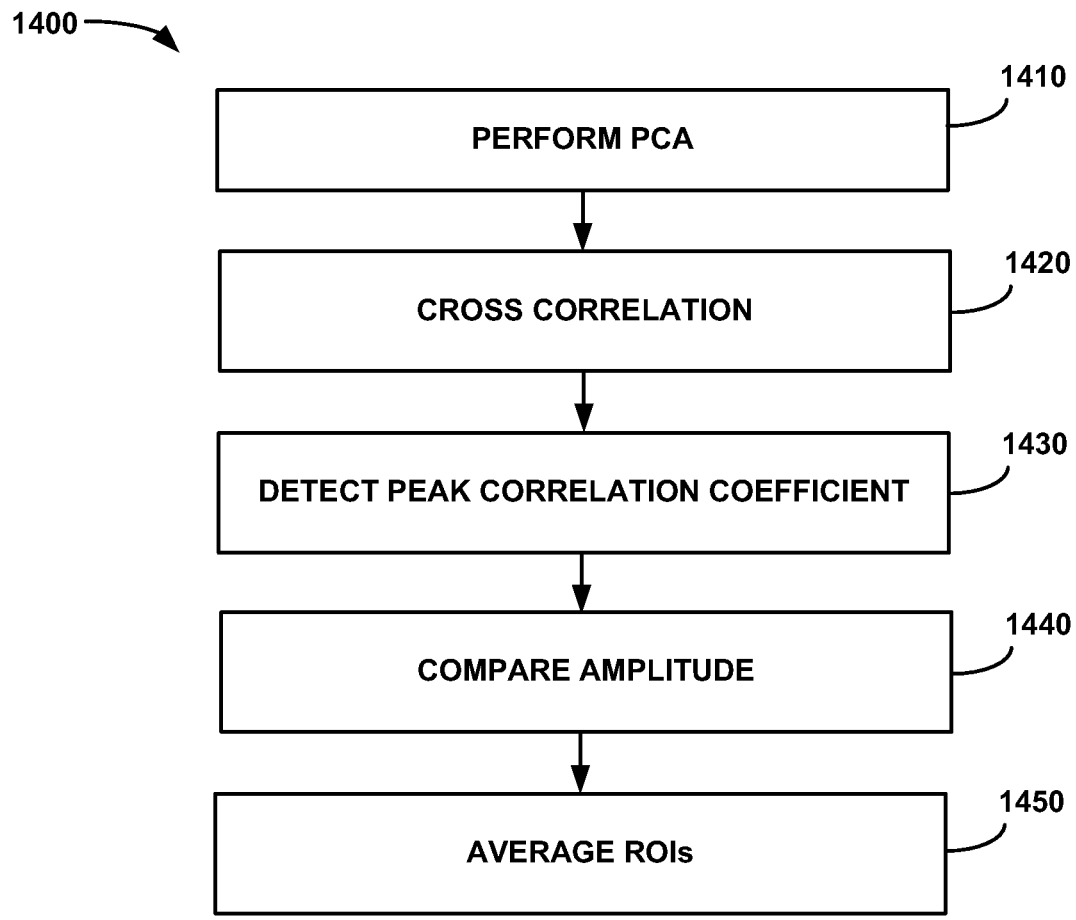
FIG. 23 illustrates another example flowchart of a method for averaging signals.

FIG. 23 illustrates another flowchart of an example method 1400 that can be implemented for averaging signals (e.g., biological electrical signals). The method 1400 can be implemented, for example by the system 2 illustrated in FIG. 1. At 1410, PCA can be performed (e.g., by the PCA function 42 illustrated in FIG. 1) on data corresponding to a subset of a plurality of signals and a selected template to generate a virtual lead and an optimized template, wherein each of the plurality of signals corresponds to an electrical biological signal detected by a sensor. At 1420 a cross correlation on the virtual lead and the optimized template can be calculated to determine a strength of linear dependence between the virtual lead and the optimized template to determine ROIs of the virtual lead. At 1430, peak correlation coefficients in the virtual lead can be detected (e.g., by the peak correlation coefficient detector 46 illustrated in FIG. 1). At 1440, the amplitude of each of the ROIs of the virtual lead can be compared (e.g., by the amplitude comparator 48 illustrated in FIG. 1) with the selected template to determine an error between the template and each ROI of the virtual lead. At 1450, the ROIs can be averaged (e.g., by the segment averaging function 50 illustrated in FIG. 1) to generate averaged data.

Figure 24:
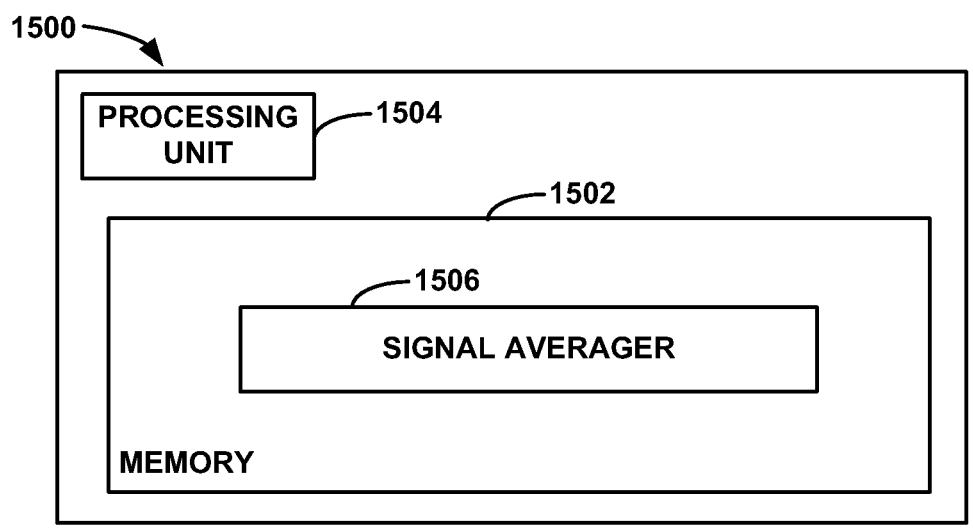
FIG. 24 illustrates another example of a system for averaging signals.

FIG. 24 illustrates another example of a system 1500 for averaging a signal. The system can comprise a memory 1502 for storing machine readable instructions and a processing unit 1504 (e.g., a processor core) to access the memory and execute the machine readable instructions. The machine readable instructions can comprise a signal averager 1506 configured to detect regions of poor signal quality for each of a plurality of signals, wherein each of the plurality of signals corresponds to a biological signal (e.g., acquired concurrently from a surface of patient's body). The signal averager 1506 can also be configured to determine which of the plurality of signals is associated with a bad channel based on the detected regions of poor signal quality. The signal averager can further be configured to provide averaged data corresponding to an average of regions of interest (ROIs) that are determined based on a strength of linear dependence between a virtual lead and an optimized template, wherein the virtual lead and the optimized template are based on the plurality of signals that are not associated with the bad channel and based on a selected template.

What have been described above are examples. It is, of course, not possible to describe every conceivable combination of components or methodologies, but one of ordinary skill in the art will recognize that many further combinations and permutations are possible. Accordingly, the disclosure is intended to embrace all such alterations, modifications, and variations that fall within the scope of this application, including the appended claims.

As used herein, the term "includes" means includes but not limited to, the term "including" means including but not limited to. The term "based on" means based at least in part on. Additionally, where the disclosure or claims recite "a," "an," "a first," or "another" element, or the equivalent thereof, it should be interpreted to include one or more than one such element, neither requiring nor excluding two or more such elements.

What is claimed is:

1. A method comprising:
   receiving measurement data characterizing a subset of a plurality of electrical biological signals detected by sensors;
   selecting a template region of the signals characterized by the measurement data;
   performing principal component analysis (PCA) on the measurement data to generate a virtual lead corresponding to a single channel representation of the subset of signals characterized by the measurement data and performing PCA on the selected template region to generate an optimized template corresponding to a single channel representation of the selected template region;
   calculating a cross correlation on the virtual lead and the optimized template to determine a strength of linear dependence between the virtual lead and the optimized template to determine regions of interest (ROIs) of the virtual lead;
   detecting peak correlation coefficients in the virtual lead based on the cross-correlation to identify potential ROIs;
   comparing the amplitude of each of the ROIs of the virtual lead with the optimized template to determine an error between the optimized template and each ROI of the virtual lead for each of the potential ROIs; and
   generating averaged data for the each of the plurality of signals by determining an average for each respective ROI of the virtual lead based on the error.

2. The method of claim 1, further comprising:
   detecting regions of poor signal quality for each of the plurality of signals; and
   determining which of the plurality of signals is associated with a bad channel based on the detected regions of poor signal quality, each bad channels being excluded from the PCA.

3. The method of claim 1, further comprising mapping the averaged data to a surface of an organ to reconstruct electrical activity of the organ.

4. The method of claim 3, further comprising generating one of potential and isochrone maps based on the mapped averaged data.

5. The method of claim 1, wherein the plurality of signals comprises at least 200 signals acquired concurrently from a body surface of a patient, the averaged data including signal averaged data computed for a subset of the at least 200 signals.

6. The method of claim 5, wherein each of the plurality of signals represents an electrocardiograph (ECG) signal.

7. The method of claim 5, wherein the template defines a P wave.

8. The method of claim 1, wherein the plurality of signals are acquired non-invasively from a patient.

9. The method of claim 1, wherein the plurality of signals are acquired invasively from a patient.

10. The method of claim 1, wherein PCA is performed on data corresponding to a sensing zone that comprises a proper subset of the plurality of signals, the averaging being performed on the plurality of signals.

11. The method of claim 1, further comprising detecting and removing correlated noise from the subset of the plurality of signals.

12. A non-transitory machine readable medium for storing machine readable instructions, the machine readable instructions comprising:
   a signal averager that receives measurement data that characterizes a plurality of concurrently detected biological signals, the signal averager comprising:
      a principal component analysis (PCA) function that performs PCA on the measurement data for a subset of the biological signals to generate a virtual lead corresponding to a single channel representation of the subset of the biological signals and performs PCA on a selected template region of the plurality of biological signals to generate an optimized template corresponding to a single channel representation of the selected template region;
      a cross correlation (CC) calculator that determines a strength of linear dependence between the virtual lead and the optimized template to determine potential regions of interest (ROIs) of the virtual lead;
      an amplitude comparator that compares the amplitude of each of the potential ROIs of the virtual lead with the optimized template to determine an error between the optimized template and each ROI of the virtual lead; and
      a segment averaging function that averages each of the ROIs based on the error between the optimized template and each ROI to calculate averaged data for each of the biological signals.

13. The non-transitory machine readable medium of claim 12, wherein the machine readable instructions further comprise a mapping system comprising:

a reconstruction component to convert the averaged data to corresponding reconstructed electrical activity of an organ of a patient; and a map generator to produce map data based on the reconstructed electrical activity of the organ of the patient.

14. The non-transitory machine readable medium of claim 12, wherein the signal averager further comprises a zone selector to select a sensing zone comprising a proper subset of the biological signals, wherein the PCA function performs the PCA on the sensing zone.

15. The non-transitory machine readable medium of claim 12, wherein the signal averager further comprises a peak correlation coefficient detector to determine maximum correlation coefficients for the virtual lead.

16. The non-transitory machine readable medium of claim 12, wherein the machine readable instructions further comprise a bad channel detector to:

detect regions of poor signal quality for each of the plurality of biological signals; and determine which of the plurality of biological signals is associated with a bad channel based on the detected regions of poor signal quality, each bad channel being identified for exclusion from the PCA function.

17. A system comprising:

a memory for storing machine readable instructions; and a processing unit to access the memory and execute the machine readable instructions, the machine readable instructions comprising:

a signal averager to:

detect regions of poor signal quality for each of a plurality of signals, wherein each of the plurality of signals corresponds to an electrical biological signal;

determine which of the plurality of signals is associated with a bad channel based on the detected regions of poor signal quality; and provide averaged data corresponding to an average of regions of interest (ROIs) that are determined based on a strength of linear dependence between a virtual lead and an optimized template, wherein the virtual lead and the optimized template are determined based on the plurality of signals that are not associated with the bad channel and based on a selected template region of the plurality of signals, and wherein the virtual lead corresponds to a single channel representation of the subset of the biological signals and the optimized template corresponds to a single channel representation of the selected template region.

18. The system of claim 17, further comprising a sensor array mounted on a substrate, the sensor array comprising a plurality of sensors, the sensor array providing the plurality of signals.

19. The system of claim 18, further comprising a graphical user interface to provide study data to the signal averager in response to user input, the study data identifying a sensing zone that comprises a proper subset of the plurality of sensors in the senor array, wherein the signal averager provides the averaged data based on signals of the plurality of signals that are provided from the proper subset of the plurality of sensors in the sensing zone.

20. The system of claim 17, further comprising a graphical user interface that provides an interface for selecting the template in response to user input.

* * * * *